(12) United States Patent
Borenstein et al.

(10) Patent No.: US 9,457,138 B2
(45) Date of Patent: Oct. 4, 2016

(54) MICROFABRICATED ARTIFICIAL LUNG ASSIST DEVICE, AND METHODS OF USE AND MANUFACTURE THEREOF

(71) Applicant: The Charles Stark Draper Laboratory, Inc., Cambridge, MA (US)

(72) Inventors: Jeffrey T. Borenstein, Newton, MA (US); Joseph L. Charest, Cambridge, MA (US); James Ching-Ming Hsiao, Watertown, MA (US); Tatiana Kniazeva, Amherst, NH (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 96 days.

(21) Appl. No.: 14/177,799

(22) Filed: Feb. 11, 2014

(65) Prior Publication Data

US 2014/0193799 A1 Jul. 10, 2014

Related U.S. Application Data

(63) Continuation of application No. 13/116,219, filed on May 26, 2011, now Pat. No. 8,647,410.

(60) Provisional application No. 61/348,563, filed on May 26, 2010.

(51) Int. Cl.
| | |
|---|---|
| *B01D 53/22* | (2006.01) |
| *A61M 1/16* | (2006.01) |
| *B01D 63/08* | (2006.01) |

(52) U.S. Cl.
CPC .......... *A61M 1/1698* (2013.01); *B01D 63/081* (2013.01); *B01D 63/082* (2013.01); *B01D 63/084* (2013.01); *B01D 63/088* (2013.01); *B01D 71/70* (2013.01); *A61M 1/3643* (2013.01)

(58) Field of Classification Search
CPC ............ A61M 1/1698; A61M 1/3643; B01D 63/081; B01D 63/082; B01D 63/084; B01D 63/088; B01D 71/70
See application file for complete search history.

(56) References Cited

U.S. PATENT DOCUMENTS

| | | | |
|---|---|---|---|
| 2,876,769 A | 3/1959 | Cordova | |
| 2,985,588 A * | 5/1961 | Binning | B01D 61/362 208/308 |

(Continued)

FOREIGN PATENT DOCUMENTS

| | | |
|---|---|---|
| DE | 102008045621 A1 | 3/2010 |
| EP | 0 041 62 | 12/1981 |

(Continued)

OTHER PUBLICATIONS

"King Saud University "Reverse Osmosis" pp. 409-452, Sep. 30, 2010, http://faculty.ksu.edu.sa/Almutaz/Documents/ChE-413/Reverse%20Osmosis.pdf".*

(Continued)

*Primary Examiner* — Anthony Shumate
(74) *Attorney, Agent, or Firm* — Edward A. Gordon; Foley & Lardner LLP

(57) ABSTRACT

The invention provides systems and methods for exchanging gas in an oxygenator device, and methods for preparing and using such oxygenator devices. The systems and methods can be used to transfer oxygen to blood to assist lung function in a patient.

10 Claims, 13 Drawing Sheets

(56) References Cited

U.S. PATENT DOCUMENTS

| | | | |
|---|---|---|---|
| 3,489,647 A | | 1/1970 | Kolobow |
| 3,738,813 A | | 6/1973 | Esmond |
| 3,834,544 A | * | 9/1974 | Tyson, Jr. ............ A61M 1/1698 210/321.75 |
| 3,847,211 A | | 11/1974 | Fischel et al. |
| 4,075,091 A | * | 2/1978 | Bellhouse ............. B01D 61/28 210/637 |
| 4,415,447 A | * | 11/1983 | Foucras ............... B01D 63/084 210/321.6 |
| 4,583,969 A | * | 4/1986 | Mortensen .......... A61M 1/1678 261/122.1 |
| 4,620,965 A | | 11/1986 | Fukusawa et al. |
| 4,756,835 A | | 7/1988 | Wilson |
| 4,997,565 A | | 3/1991 | Niesen |
| 5,120,445 A | | 6/1992 | Colman |
| 5,192,320 A | * | 3/1993 | Anazawa .......... B01D 67/0025 623/23.65 |
| 5,207,639 A | | 5/1993 | Cooper |
| 5,254,259 A | * | 10/1993 | Bellhouse ............... A61M 5/44 210/320 |
| 5,338,770 A | * | 8/1994 | Winters .............. A61L 33/0005 523/112 |
| 5,411,650 A | * | 5/1995 | Frank .................... B01D 61/52 204/518 |
| 6,241,945 B1 | | 6/2001 | Owen |
| 6,416,666 B1 | * | 7/2002 | Salyer .................... B01D 63/16 210/321.63 |
| 6,514,412 B1 | | 2/2003 | Insley et al. |
| 6,602,468 B2 | | 8/2003 | Patterson et al. |
| 7,569,144 B2 | * | 8/2009 | De Biran ............. B01D 63/082 210/321.6 |
| 7,713,544 B2 | | 5/2010 | Chaikof et al. |
| 7,759,113 B2 | | 7/2010 | Vacanti et al. |
| 7,955,504 B1 | | 6/2011 | Jovanovic et al. |
| 8,128,822 B2 | | 3/2012 | Browning et al. |
| 8,137,554 B2 | | 3/2012 | Jovanovic et al. |
| 8,266,791 B2 | | 9/2012 | Borenstein et al. |
| 8,647,410 B2 | * | 2/2014 | Borenstein .......... A61M 1/1698 422/45 |
| 8,728,214 B2 | * | 5/2014 | Maurer ............... A61M 1/1698 422/48 |
| 9,180,239 B2 | * | 11/2015 | Borenstein .......... A61M 1/1698 |
| 2002/0182241 A1 | | 12/2002 | Borenstein et al. |
| 2003/0064003 A1 | * | 4/2003 | Takehisa ............. A61M 1/1698 422/45 |
| 2003/0121841 A1 | | 7/2003 | Harttig et al. |
| 2003/0175149 A1 | | 9/2003 | Searles et al. |
| 2005/0202557 A1 | | 9/2005 | Borenstein et al. |
| 2006/0136182 A1 | | 6/2006 | Vacanti et al. |
| 2006/0173394 A1 | | 8/2006 | Stroock et al. |
| 2007/0119771 A1 | | 5/2007 | Schukar et al. |
| 2008/0093298 A1 | | 4/2008 | Browning et al. |
| 2009/0081079 A1 | | 3/2009 | Johns |
| 2009/0098017 A1 | * | 4/2009 | Celik-Butler ........... A61M 1/16 422/48 |
| 2009/0234332 A1 | | 9/2009 | Borenstein et al. |
| 2010/0098742 A1 | | 4/2010 | Vacanti et al. |
| 2010/0118642 A1 | | 5/2010 | Ho et al. |
| 2010/0267136 A1 | | 10/2010 | Vacanti et al. |
| 2011/0158847 A1 | | 6/2011 | Charest et al. |
| 2011/0186165 A1 | | 8/2011 | Borenstein et al. |
| 2011/0226686 A1 | | 9/2011 | Maurer |
| 2011/0290113 A1 | * | 12/2011 | Borenstein .......... A61M 1/1698 95/54 |
| 2012/0182609 A1 | | 7/2012 | Borenstein et al. |
| 2013/0144266 A1 | * | 6/2013 | Borenstein .......... A61M 1/1698 604/522 |
| 2013/0197420 A1 | * | 8/2013 | Fissell, IV .......... A61M 1/1698 604/6.16 |
| 2014/0150662 A1 | * | 6/2014 | Vandermeulen .......... F28F 1/02 96/295 |
| 2014/0255253 A1 | * | 9/2014 | Fusch ................. A61M 1/1698 422/48 |

FOREIGN PATENT DOCUMENTS

| | | |
|---|---|---|
| GB | 1 408 562 | 10/1975 |
| JP | 2003-093853 | 4/2003 |
| WO | WO-02/076529 A1 | 10/2002 |
| WO | WO-2006/042079 A1 | 4/2006 |
| WO | WO-2010/025926 | 3/2010 |
| WO | WO-2011/150216 | 12/2011 |
| WO | WO-2011/150216 A1 | 12/2011 |

OTHER PUBLICATIONS

First Office Action issued on Jul. 17, 2014 in Chinese Patent Application No. 2011800367123, 13 pages.
Patent Examination Report No. 1 in Australian Patent Application No. 2011258203, 2 pages.
US Office Action in U.S. Appl. No. 13/705,795 DTD Oct. 22, 2014, 12 pages.
Office Action issued Dec. 4, 2014 in Japanese Patent Application No. 2012-547304, 6 pages.
US Notice of Allowance in U.S. Appl. No. 12/981,903 DTD Feb. 2, 2015, 7 pages.
International Search Report and Written Opinion mailed Jul. 17, 2015 in PCT Application No. PCT/US2015/027321, 10 pages.
International Preliminary Report on Patentability mailed on Jun. 19, 2014 in PCT Application No. PCT/US2012/067971, 8 pages.
Stroock, et al., "Chaotic Mixer for Microchannels", Science, vol. 295, Jan. 25, 2002, pp. 647-651.
US Office Action in U.S. Appl. No. 12/981,903 dated Jul. 30, 2014, 22 pages.
US Office Action in U.S. Appl. No. 13/705,795 dated May 16, 2014, 16 pages.
Borenstein et al., "Microfabrication Technology for Vascularized Tissue Engineering," Biomedical Microdevices, 4(3):167-175 (2002).
Burgess et al., "Towards Microfabricated Biohybrid Artificial Lung Modules for Chronic Respiratory Support," Biomedical Microdevices, 11(12):117-127 (2008).
Wu et al., "Construction of Microfluidic Chips Using Polydimethylsiloxane for Adhesive Bonding," Lab on a Chip, 5:1393-1398 (2005).
International Preliminary Report on Patentability in PCT/US2010/062537, dated Jul. 12, 2012, 8 pages.
International Preliminary Report on Patentability in PCT/US2011/038148, dated Dec. 6, 2012, 9 pages.
International Search Report and Written Opinion in PCT/US2012/067971, dated Mar. 12, 2013, 12 pages.
International Search Report in PCT/US2010/062537, dated May 2, 2011, 5 pages.
International Search Report in PCT/US2011/038148, dated Aug. 26, 2011, 4 pages.
Kuo, Alex C. M., Poly (dimethylsiloxane), Polymer data handbook, 1999 Oxford University Press, Inc., 25 pages.
LeClerc et al., "Cell Culture in 3-Dimensional Microfluidic Structure of PDMS (polydimethylsiloxane)," Biomedical Microdevices, 5(2):109-114 (2003).
Notice of Allowance in U.S. Appl. No. 13/116,219 dated Oct. 4, 2013, 23 pages.
Office Action in U.S. Appl. No. 12/981,903 dated Sep. 11, 2013, 19 pages.
US Notice of Allowance in U.S. Appl. No. 13/116,219, dated Jun. 14, 2013, 9 pages.
US Office Action in U.S. Appl. No. 12/981,903, dated Aug. 30, 2012, 16 pages.
US Office Action in U.S. Appl. No. 12/981,903, dated Feb. 22, 2013, 17 pages.
Yasuda, H. "Units of Gas Permeability Constants", Journal of Applied Polymer Science, 1975, vol. 19, pp. 2529-2536.
Office Action issued Mar. 26, 2015 in Japanese Patent Application No. 2013-512244, 8 pages.
US Notice of Allowance in U.S. Appl. No. 12/981,903 DTD May 19, 2015, 8 pages.

US Office Action in U.S. Appl. No. 13/705,795 DTD Mar. 13, 2015, 13 pages.
Chinese Search Report dated Oct. 26, 2015 for Chinese Patent Application No. 2012800595919, 2 pgs.
First Office Action dated Nov. 4, 2015 for Chinese Patent Application No. 2012800595919 (with English Translation), 17 pgs.

US Notice of Allowance in U.S. Appl. No. 13/705,795 dated Aug. 19, 2015, 9 pgs.
US Notice of Allowance on U.S. Appl. No. 13/705,795 dated Oct. 7, 2015, 6 pgs.

* cited by examiner

Figure 1
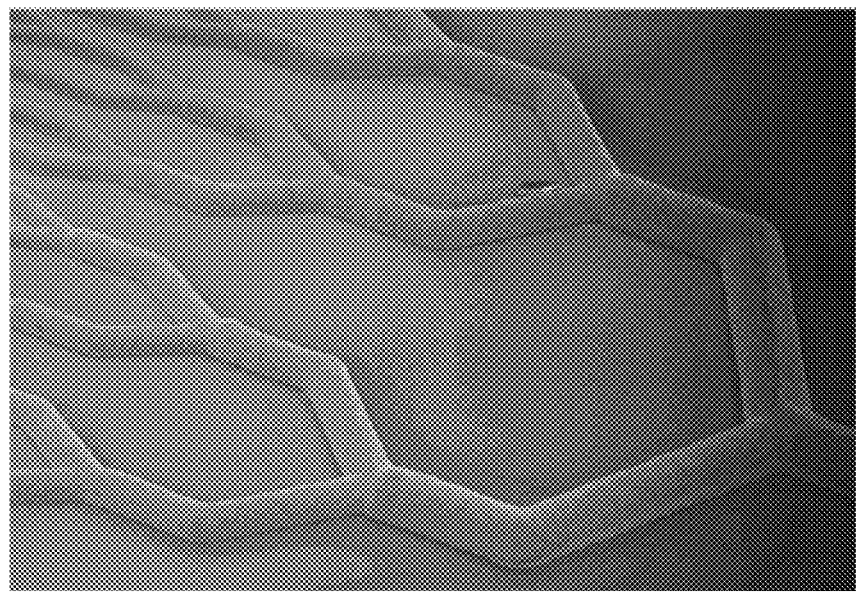
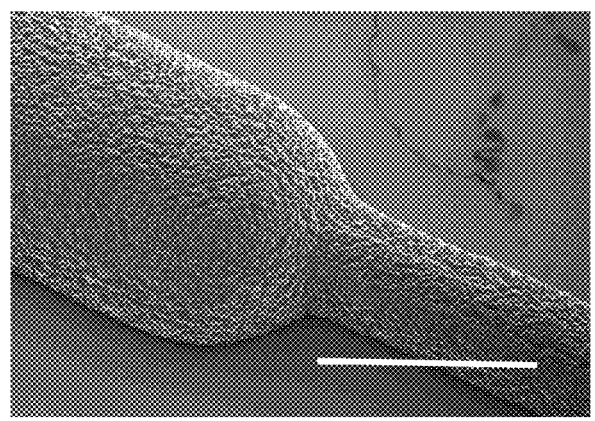

Figure 7
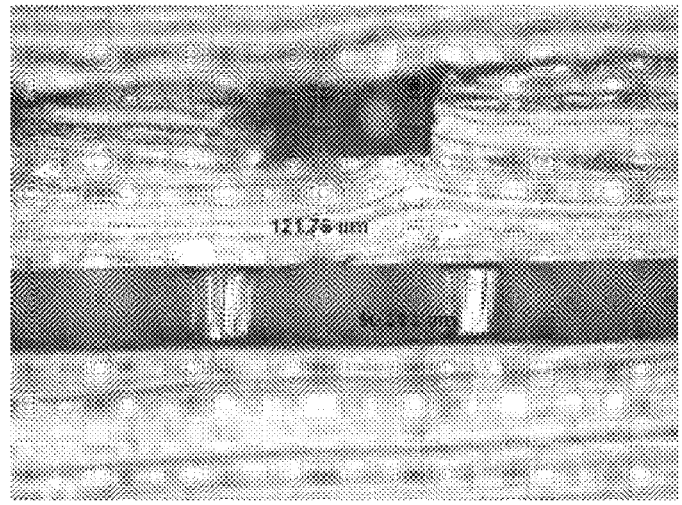
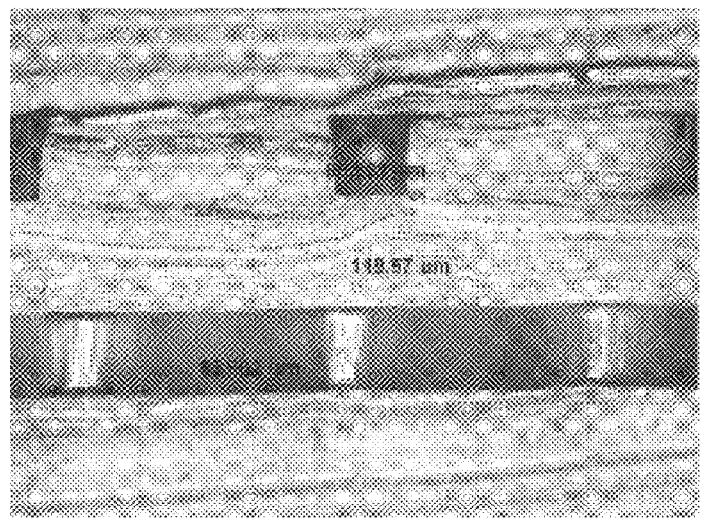

MICROFABRICATED ARTIFICIAL LUNG ASSIST DEVICE, AND METHODS OF USE AND MANUFACTURE THEREOF

RELATED APPLICATIONS

This application is a continuation of U.S. Pat. No. 8,647, 410, filed May 26, 2011, and titled "Microfabricated Artificial Lung Assist Device, and Methods Of Use and Manufacture Thereof," which claims the benefit of and priority to U.S. Provisional Patent Application No. 61/348,563, filed May 26, 2010, both of which are hereby incorporated by reference.

GOVERNMENT SUPPORT

This invention was made with support provided by the National Institutes of Health (Grant No. R21 HL106585-01); therefore, the government has certain rights in the invention.

FIELD OF THE INVENTION

The invention provides systems and methods for exchanging gas in an oxygenator device, and methods for preparing and using such oxygenator devices.

BACKGROUND OF THE INVENTION

Acute and chronic diseases of the lungs affect one of the broadest patient populations and represent some of the most urgent and unmet health care needs. Acute illnesses of the lungs include neonatal conditions related to incompletely developed lungs, severe infections, burns and other lung injuries, and Acute Respiratory Distress Syndrome (ARDS). These conditions are often treated using mechanical ventilation to sustain patient oxygen levels while the lungs recover. In intensive-care and emergency settings, oxygenation is often accomplished by ventilation. However, this method requires functioning lungs and often results in mechanical trauma or infection.

Chronic diseases of the lungs include chronic obstructive pulmonary disease (COPD), cystic fibrosis (CF), mesothelioma, and lung cancer. Chronic insufficient oxygenation is typically treated using portable oxygen therapy, which still depends on oxygen transfer to the blood stream across diseased or damaged lungs, and does not address the underlying condition. Pharmacologic therapies are also used, but have limited effectiveness.

Since portable oxygen therapy, mechanical ventilation, and similar approaches generally require functioning lungs to achieve oxygenation and carbon dioxide removal, patients with damaged or diseased lungs are often barely sustained by these methods. In the typical course of events, patients have severe limits of exertion placed upon them, since their oxygen levels are insufficient even for sustaining resting requirements. As the patients' lungs continue to fail, limits on their activity and their overall health become more severe, with many acute exacerbations and hospitalizations and a steadily worsening prognosis.

More advanced treatments for lung failure have been developed over the past few decades. Currently, patients suffering from cardiac and pulmonary failure may be treated with a therapy known as extracorporeal membrane oxygenation (ECMO), which effectively bypasses the lungs. ECMO is used frequently in neonates and children. ECMO technology exists in several configurations, including hollow fiber-based systems, planar or flat sheet configurations, and spiral or wound systems. Typically, these devices include an oxygenator as the central component of the system, along with heat exchangers, bubble traps, fluid circuitry, pumps, and other components.

In ECMO, blood is typically pumped from the internal jugular vein through an oxygenation device, and back into the carotid artery. (In an alternative to this venous-arterial circuit, a veno-venous circuit may also be used, depending on the needs of the patient.) More particularly, in typical devices, blood is drained from the venous supply into a reservoir, or bladder, and the tubing, typically made from materials such as PVC or Tygon, leads to the actual ECMO pump (often a roller pump). The pump, in turn, drives the blood through a membrane oxygenator, which transfers oxygen into the blood and removes carbon dioxide across the membrane. In one implementation, the membrane oxygenator is formed by a flat, thin silicone-rubber membrane stretched across a plastic frame, and is often rolled into a cylinder. The pumping process typically results in a lowering of the blood temperature, and, therefore, a heat exchanger is often used to maintain body temperature. The blood pressure is carefully monitored in this system, as are the oxygen and $CO_2$ levels in the blood. Detection of bubbles, in order to prevent an air embolism, is another generally important element of the system. In order to avoid clotting, large doses of anti-coagulants such as heparin may be provided.

In one common, fiber-based oxygenation configuration, blood is channeled outside hollow fibers of a fiber bundle, while oxygen is passed through the lumens of the fibers. Generally, the fibers are porous, and therefore some plasma leakage occurs, but blood proteins quickly block significant leakage through a combination of physical and surface energy mechanisms. In some instances, the fibers are coated with a film of silicone to prevent plasma leakage. One older technology utilizes flat sheet membranes stacked in a planar configuration. Limitations on conventional fabrication technologies for such devices severely limit the device performance. For instance, limitations on the membrane thickness, channel depth, width of spacers between parallel channels, and flow paths in the manifold collectively limit the ability to miniaturize and inexpensively manufacture systems with high gas transfer rates.

The non-physiologic nature of the ECMO circuit also imposes certain disadvantages. Because blood is oxygenated through a large compartment, fluid forces acting on the blood differ substantially from those in alveolar capillaries. These differences can lead to inflammatory responses that increase morbidity and mortality in ECMO, both in neonatal and pediatric populations. In addition, anomalous flow paths and contact between blood and artificial materials such as PVC, Tygon, and silicone rubber can cause a high incidence of clotting, unless large doses of anticoagulants are supplied. These anticoagulants, such as heparin, can lead to complications such as excessive bleeding and electrolyte-related imbalances. The deleterious blood surface interactions that lead to coagulation in artificial organ assist device systems can be reduced by selecting materials with high hemocompatibility, but adverse interactions are often unavoidable. Therefore, reduced surface areas are highly desired.

In addition to therapeutic applications for treatment of disease, cardiopulmonary support is typically required for surgical procedures such as Coronary Artery Bypass Graft (CABG), where the patient is placed on a bypass pump circuit that oxygenates the blood during the operation. Over 500,000 of these operations are done annually in the United States alone. Current membrane oxygenator technology for CABG procedures generally require very large prime volumes of blood in the device (i.e., large blood volumes to fill the device) and significant anticoagulation, and typically include complex circuitry that necessitates highly trained perfusionists to operate. Large prime volumes result, for example, from limitations in the smallest diameter or other critical dimensions of hollow fibers or flat sheet systems. They often lead to a need for blood transfusions and for a large percentage of the patient's blood to be outside the body at any given time during the treatment. Conventional ECMO devices typically also require a large surface area. The surface area is driven by the requirement for sufficient oxygen and carbon dioxide transfer rates, and sufficiently high rates generally require very large surface area, in particular if the gas transfer membrane is thick. Larger surface areas, in turn, lead to larger systems, more expensive material costs, and more extensive problems with blood-surface interactions.

Accordingly, there is a need for improved ECMO devices that facilitate high oxygen transfer rates with smaller prime volumes and surface areas, and that are less prone to coagulation and inflammation. The present invention addresses this need and provides other related advantages.

SUMMARY

The invention provides extracorporeal membrane oxygenator devices, methods for manufacturing such devices, and methods for facilitating gas exchange with a fluid. The extracorporeal membrane oxygenator devices may be used in medical applications where it is desirable to transfer a gas to or from a fluid. For example, the devices and methods described herein are contemplated to provide particular advantages in transferring oxygen to blood and to be applicable for use as an artificial lung device. One advantage provided by devices described herein is that they require only minimal amounts of blood to prime the device. Another advantage of devices described herein is that channels for blood flow are configured to provide superior fluid flow properties, thereby minimizing the risk of blood clots while reducing reliance on anticoagulants.

One exemplary collection of devices described herein contain at least one first micropatterned polymer layer containing channels for blood flow, at least one second micropatterned polymer layer containing channels for gas flow, and a gas-permeable polymer membrane separating the first micropatterned polymer layer from the second micropatterned polymer layer. The gas-permeable membrane provided herein is thin in order to maximize gas transfer, and yet the gas-permeable membrane is sufficiently robust to withstand forces applied to the membrane as blood flows through the oxygenator device. Features of the channels in the first micropatterned polymer layer, such as height, width, length, and arrangement can be optimized to maximize transfer of gas to and/or from blood, and also provide superior blood flow properties for transmission of blood through the device. The first micropatterned polymer layer, second micropatterned polymer layer, and gas-permeable membrane are desirably bonded together to form a bi-layer, and a plurality of such bi-layers can be arranged in a stack.

Accordingly, one aspect of the invention provides an extracorporeal membrane oxygenator device, comprising a plurality of bi-layer structures arranged in a stack, each bi-layer structure comprising (i) a first micropatterned polymer layer defining a microvascular network for blood flow therethrough; (ii) a second micropatterned polymer layer defining channels for gas supply; and (iii) a gas-permeable polymer membrane located between and bonding the first micropatterned polymer layer to the second micropatterned polymer layer.

Another aspect of the invention provides a method for transferring a gas to blood, comprising passing blood through a device described herein having a gas in at least one channel for gas flow, to thereby transfer said gas to the blood.

Another aspect of the invention provides a method of manufacturing a bi-layer structure for use in an extracorporeal membrane oxygenator device, the structure including first and second micropatterned polymer layers and a gas-permeable polymer membrane therebetween. The method comprises spin-coating a prepolymer mixture onto a silicon wafer so as to form the polymer membrane, the polymer membrane being attached to the silicon wafer at a first side of the polymer membrane; bonding the first micropatterned polymer layer to a second side of the polymer membrane; releasing the polymer membrane from the silicon wafer; and bonding the second micropatterned polymer layer to the first side of the polymer membrane. Thickness of the polymer membrane can be controlled by adjusting the spinning speed of the silicon wafer during the spin-coating step. In addition, thickness of the polymer membrane can be controlled by adjusting the viscosity of the prepolymer mixture, such as where the prepolymer mixture comprises a solvent that reduces the viscosity of the prepolymer mixture.

A further aspect of the invention provides a method of manufacturing a bi-layer structure for use in an extracorporeal membrane oxygenator device, the structure including first and second micropatterned polymer layers and a gas-permeable polymer membrane therebetween. The method comprises spin-coating a prepolymer mixture onto a micropatterned silicon wafer so as to fill recessed features of the micropatterned silicon wafer and form a thin, continuous polymer layer thereover, thereby forming an integrated structure including the first micropatterned polymer layer and the gas-permeable polymer membrane; releasing the integrated structure from the silicon wafer; and bonding the second micropatterned polymer layer to the exposed side of the gas-permeable polymer membrane.

These and other aspects, along with other features and embodiments of the invention herein disclosed herein, will become more apparent through reference to the following description, drawings, and claims. Furthermore, it is to be understood that the aspects, features, and embodiments described herein are not mutually exclusive and can exist in various combinations and permutations.

BRIEF DESCRIPTION OF FIGURES

FIG. 1 is an illustration of rounded channels.

FIG. 7 illustrates devices fabricated using techniques described herein.

FIG. 9 illustrates features of an oxygenator device described in Example 1.

DETAILED DESCRIPTION

Figure 2:
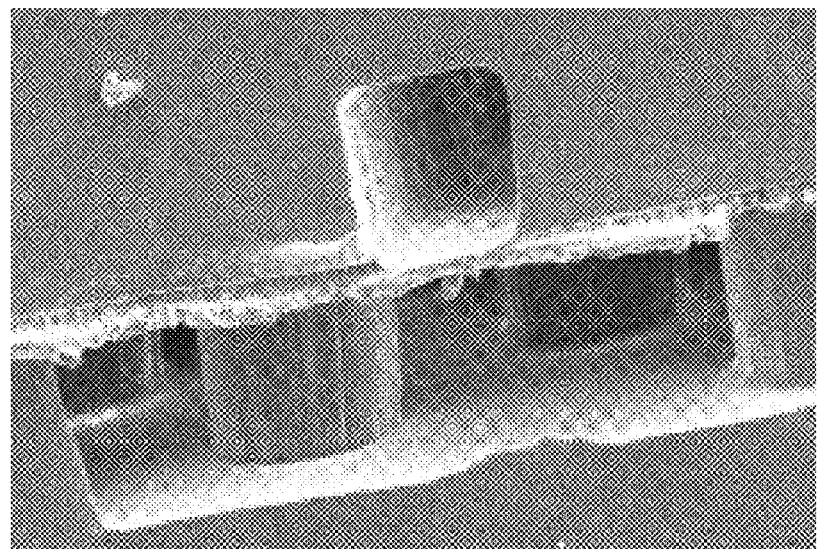
FIG. 2 is an illustration of a post pattern architecture in a microvascular channel formed in polydimethylsiloxane.

The invention provides extracorporeal membrane oxygenator devices, methods for manufacturing such devices, and methods for facilitating gas exchange with a fluid. As explained above, the extracorporeal membrane oxygenator devices may be used in medical applications where it is desirable to transfer a gas to and/or from a fluid. The extracorporeal membrane oxygenator devices and methods are contemplated to provide particular advantages in transferring oxygen to blood and to be applicable for use in an artificial lung device. For example, the thin gas-permeable membrane provides superior gas transfer, and yet is sufficiently robust to withstand forces applied to the membrane as blood flows through the oxygenator device. Further, features of the channels for fluid flow described herein are contemplated to reduce the occurrence of blood clotting, hemolysis, inflammation, and other side effects that a patient may experience due to use of a lung assist gas exchange device. Also, the configuration of the device requires only minimal blood to prime the device.

Various aspects of the invention are set forth below in sections; however, aspects of the invention described in one particular section are not to be limited to any particular section.

I. GENERAL FEATURES OF THE EXTRACORPOREAL MEMBRANE OXYGENATOR DEVICES

Devices described herein contain at least one first micropatterned polymer layer containing channels for blood flow, at least one second micropatterned polymer layer containing channels for gas flow, and a gas-permeable polymer membrane separating the first micropatterned polymer layer from the second micropatterned polymer layer. The gas-permeable polymer membrane located between the two polymer layers serves to fluidically separate the layers while providing gas exchange therebetween, and further bonds the layers to one another (e.g., by bonding the layers to the two sides of the membrane). The gas-permeable membrane is typically very thin in order to maximize gas transfer between fluid in channels in the first micropatterned polymer layer and gas in channels in the second micropatterned polymer layer. The gas-permeable membrane should be sufficiently robust to withstand forces applied to the membrane as blood flows through the oxygenator device. Further, the gas-permeable membrane desirably does not permit any significant amount of liquid (e.g., blood proteins or water) to pass through the membrane. Features of the channels in the first micropatterned polymer layer, such as height, width, length, and arrangement can be optimized to maximize transfer of gas to and/or from blood, and also provide superior fluid flow properties for transmission of blood through the device.

The first micropatterned polymer layer, second micropatterned polymer layer, and gas-permeable membrane are desirably bonded together to form a bi-layer, and a plurality of such bi-layers can be arranged in a stack. To facilitate fluid communication between the bi-layers, holes may be punched through the stacked layers to provide for communication between channels for blood flow (e.g., a microvascular network in a bi-layer) and channels for gas flow (e.g., oxygen-supply channels in the second micropatterned polymer layer). Alternatively, a distribution manifold, which may be formed of two polymer layers defining mirror-symmetric bifurcated channel networks, may connect the channel ports of bi-layers in the device.

Accordingly, one aspect of the invention provides an extracorporeal membrane oxygenator device, comprising (i) a first micropatterned polymer layer defining channels for blood flow; (ii) a second micropatterned polymer layer defining channels for gas supply; and (iii) a gas-permeable polymer membrane located between and bonding the first micropatterned polymer layer to the second micropatterned polymer layer. Channels for blood flow in the first micropatterned polymer layer may be arranged in the form of a microvascular network. Thus, in certain embodiments, the invention provides an extracorporeal membrane oxygenator device, comprising a plurality of bi-layer structures arranged in a stack, each bi-layer structure comprising: (i) a first micropatterned polymer layer defining a microvascular network for blood flow therethrough; (ii) a second micropatterned polymer layer defining channels for gas supply; and (iii) a gas-permeable polymer membrane located between and bonding the first micropatterned polymer layer to the second micropatterned polymer layer.

Various aspects of the first micropatterned polymer layer, the second micropatterned polymer layer, and the gas-permeable membrane are described below.

A. Features of the First Micropatterned Polymer Layer

Devices described herein contain at least one first micropatterned polymer layer containing channels for blood flow. Channels in the first micropatterned polymer layer can be arranged to provide a network of interconnecting channels. The network of interconnecting channels may contain bifurcations or other geometries to direct blood flow through the channels. Accordingly, in certain embodiments, channels in the first micropatterned polymer layer define a microvascular network for blood flow. In other embodiments, channels in the first micropatterned polymer layer may run approximately parallel to each other in the device.

Channels in the first micropatterned polymer layer may have cross-sections that are rectangular, triangular, round, or other geometries. In certain embodiments, channels in the first micropatterned polymer layer have cross-sections that are rectangular. In certain embodiments, channels in the first micropatterned polymer layer are hemispherical or rounded. Rounded channels are illustrated in FIG. 1. This architecture can, in some embodiments, enhance hemocompatibility and eliminate the presence of flow anomalies at sharp corners at the bottom of the blood flow channels.

Channels in the first micropatterned polymer layer can be molded in a polymeric material such as polystyrene, polycarbonate, a silicone (e.g., polydimethylsiloxane), polymethylmethacrylate, cyclic olefin copolymer (e.g., ZEONOR), polysulfone, or polyurethane. For certain applications (e.g., implantable applications), the use of biodegradable or biocompatible materials, such as polyglycerol sebacate, polyoctanediol citrate, polydiol citrate, silk fibroin, polyesteramide, and/or polycaprolactone may be advantageous. In certain embodiments, the first micropatterned polymer layer is made of a gas-permeable material.

In certain embodiments, the first micropatterned polymer layer is made of a gas-permeable silicone. In certain embodiments, the first micropatterned polymer layer is made of phenyl vinyl methyl siloxane, vinyl methyl siloxane, or fluorosilicone. In certain embodiments, the first micropatterned polymer layer is made of the silicone material Cosmesil K10 (produced by Cosmedica Ltd, Cardiff, United Kingdom) or the silicone material MDX4-4210 (produced by Dow Corning Corporation, Midland, Mich., as a mixture containing 55.0-75.0 wt % dimethylvinyl-terminated dimethylsiloxane and 15.0-35 wt % trimethylated silica). In certain embodiments, first micropatterned polymer layer is made of polydimethylsiloxane.

Channel Dimensions and Arrangement

Dimensions of channels in the first micropatterned polymer layer can be characterized according to their height, width, and length. Certain channel dimensions provide superior performance for transferring gas to and/or from blood. For example, a channel height of less than 120 μm, and even more preferably a height of about 50 μm has been found to be superior for facilitating gas exchange to the entirety of the fluid channel, due to the reduced travel distance required to oxygenate fluid in the deepest part of the channel. The height of channels in the first micropatterned polymer layer impacts, for example, (i) distance between the gas-permeable membrane and blood in the portion of the channel distal to the gas-permeable membrane and (ii) fluid flow properties (e.g., shear rates for blood transport and fluid pressure drop) as blood travels through the oxygenator device.

Accordingly, in certain embodiments, channels in the first micropatterned polymer layer have a height of not more than 120 μm, 100 μm, 75 μm, or 50 μm. In certain other embodiments, channels in the first micropatterned polymer layer have a height of not more than 120 μm. In certain other embodiments, channels in the first micropatterned polymer layer have a height in the range of 10 μm to 25 μm, about 10 μm to about 150 μm, about 20 μm to about 150 μm, about 30 μm to about 120 μm, about 40 μm to about 110 μm, about 50 μm to about 100 μm, about 30 μm to about 70 μm, about 40 μm to about 60 μm, about 45 μm to about 55 μm, about 75 μm to about 110 μm, about 90 μm to about 110 μm, or about 95 μm to about 105 μm. In certain other embodiments, channels in the first micropatterned polymer layer have a height of about 50 μm. In certain other embodiments, channels in the first micropatterned polymer layer have a height of about 40 μm to about 60 μm.

In certain embodiments, channels have variable heights, which can be made using techniques such as xenon difluoride etching or electroplating to produce silicon masters for polymer molding. These variable-height channels not only enhance hemocompatibility and potentially reduce coagulation, but may also increase gas transfer rates and the oxygenator efficiency. Transitions between channels and at points where the width or height is varied may be produced with ramps or tapers, using xenon difluoride etching, electroplating, ultrasonic machining, or other techniques capable of varying the geometry in a smooth and continuous way. Introduction of these ramps and tapers enables smooth blood flow and reduces the potential for anomalies such as eddy currents, turbulence, or blood damage.

Channels in the first micropatterned polymer layer desirably have a width in the range of about 50 μm to about 1.5 mm. In certain other embodiments, channels in the first micropatterned polymer layer have a width in the range of about 50 μm to about 150 μm, about 100 μm to about 200 μm, about 150 μm to about 250 μm, about 200 μm to about 300 μm, about 250 μm to about 350 μm, about 300 μm to about 400 μm, about 350 μm to about 400 μm, about 500 μm to about 600 μm, about 100 μm to about 500 μm, or about 50 μm to about 1 mm. Channels may have a smaller width, such as a width of 4 μm, 5 μm, 6 μm, 7 μm, 8 μm, or 9 μm. In certain other embodiments, channels have widths that vary along the channel length, which is contemplated to have a positive impact on gas transfer.

Channels in the first micropatterned polymer layer desirably have a length in the range of about 0.005 cm to about 3 cm. In certain other embodiments, channels in the first micropatterned polymer layer have a length in the range of about 0.1 cm to about 1.5 cm, about 0.5 cm to about 1.0 cm, about 0.5 cm to about 0.8 cm, or about 0.7 cm. In certain other embodiments, channels in the first micropatterned polymer layer have a length in the range of about 500 μm to about 3 cm.

The dimensions of channels in the first micropatterned polymer layer can also be characterized according ratios of height versus width, and versus length. In certain embodiments, the channels in the first micropatterned polymer layer have a height to width ratio in the range of 1:1 to about 1:6, or about 1:1 to about 1:3. In certain embodiments, channels in the first micropatterned polymer layer have height to length ratio in the range of 1:250 to about 1:800, or about 1:250 to about 1:400. In certain embodiments, channels in the first micropatterned polymer layer have width to length ratio in the range of 1:250 to about 1:800, about 1:250 to about 1:400, or about 1:250 to about 1:1.

The dimensions of channels in the first micropatterned polymer layer can also be characterized by a combination of height, width, and length ranges described above, alone or in combination with the ratios of height versus width, and versus length described above. For example, in certain embodiments, each channel in the first micropatterned polymer layer has a height in the range of about 50 μm to about 100 μm, a width in the range of about 50 μm to about 1.5 mm, and a length in the range of about 0.5 cm to about 3.0 cm. In certain embodiments, the channels in the first micropatterned polymer layer have one of the dimensions set forth in Table 1 below.

TABLE 1

| Example No. | Height (μm) | Width (μm) | Length (cm) |
|---|---|---|---|
| 1 | 40-60 | 50-150 | 0.5-0.8 |
| 2 | 40-60 | 50-150 | 0.8-1.0 |
| 3 | 40-60 | 50-150 | 1.0-2.0 |
| 4 | 40-60 | 100-200 | 0.5-0.8 |
| 5 | 40-60 | 100-200 | 0.8-1.0 |
| 6 | 40-60 | 100-200 | 1.0-2.0 |
| 7 | 90-100 | 50-150 | 0.5-0.8 |
| 8 | 90-100 | 50-150 | 0.8-1.0 |
| 9 | 90-100 | 50-150 | 1.0-2.0 |
| 10 | 90-100 | 100-200 | 0.5-0.8 |
| 11 | 90-100 | 100-200 | 0.8-1.0 |
| 12 | 90-100 | 100-200 | 1.0-2.0 |

As indicated above, in certain embodiments, one or more channels in the first micropatterned polymer layer are part of a network of interconnecting channels. The interconnecting channels may be arranged in a form that is biomimetic, i.e., a form that produces smooth fluid flow and minimizes clotting and/or an inflammatory response in blood passing through the channels. Thus, in certain preferred embodiments, the first micropatterned polymer layer contains a microvascular network that is biomimetic. Desirably, angles at which channels branch in the microvascular network and the ratios of channel dimensions for channels in the microvascular network mimic branching vascular structures that occur in human vasculature. In the context of microvascular networks that are biomimetic, one embodiment provides that the height of channels in the first micropatterned polymer layer are about 50 μm to about 100 μm. In certain other embodiments, at least 90% by volume of the channels in the network have a width in the range of about 50 μm to about 900 μm.

In certain embodiments, channels in the first micropatterned polymer layer are significantly shallower (i.e., have smaller channel heights) than those typically found in prior ECMO devices. For example, in certain embodiments, the channel heights range from about 10 μm to about 50 μm, giving rise to very short oxygen transfer distances. By contrast, conventional hollow-fiber oxygenators are limited, by the mechanical integrity of the fiber and by resistive losses that occur due to the extremely long length of the fiber relative to its diameter, to diameters of, typically, 250 μm or larger, which results in a long diffusive path for oxygen transfer from the gas compartment into the blood. Parallel-plate oxygenators described in the literature can have smaller channel heights, but the minimum height has, in the past, been limited due to planarity issues, construction challenges, and the inability to provide narrow blood flow paths that would prevent "bottoming out" of the membrane on the surface of the blood chamber.

In certain embodiments, channels in the first micropatterned polymer layer are both shallower and narrower than conventional parallel-plate or hollow-fiber technologies and are capable of providing additional control over boundary layers and enhancing gas transport. Narrower channels reduce the amount of unsupported area of the membrane—reducing the amount of unsupported membrane increases device mechanical integrity for a given membrane strength or modulus, thereby enabling the use of thinner membranes and reducing the limitations of membrane material selection imposed by mechanical integrity requirements. Moreover, in bifurcated networks, these shallow, narrow channels can readily be integrated into microfluidic pathways with tunable, biomimetic fluidic resistance values—a level of control not achievable with hollow-fiber bundles that have a fixed diameter throughout.

Shear Rate

Channels in the first micropatterned polymer layer can be characterized according to the fluid shear rate observed as a solution travels through the channels. In certain embodiments, channels in the first micropatterned polymer layer are characterized as having a fluid shear rate in the range of about 100 s$^{-1}$ to about 4000 s$^{-1}$ for blood at 37.0° C., a range of about 100 s$^{-1}$ to about 3000 s$^{-1}$ for blood at 37.0° C., a range of about 400 s$^{-1}$ to about 2200 s$^{-1}$ for blood at 37.0° C., a range of about 1000 s$^{-1}$ to about 2200 s$^{-1}$ for blood at 37.0° C., a range of about 1500 s$^{-1}$ to about 2200 s$^{-1}$ for blood at 37.0° C., or a range of about 1900 s$^{-1}$ to about 2200 s$^{-1}$ for blood at 37.0° C.

Quantity of Fluid Transport

Channels in the first micropatterned polymer layer can be further characterized according to quantity of fluid that can be transported through a population of said channels. For example, in certain embodiments, a population of 5,000 to 7,000 channels in the first micropatterned polymer layer can transport blood at a rate of about 1 mL/min to about 500 mL/min, about 15 mL/min to about 150 mL/min, about 50 mL/min to about 100 mL/min, about 100 mL/min to about 150 mL/min, or about 15 mL/min to about 50 mL/min. In certain other embodiments, the device contains a plurality of channels in the first micropatterned polymer layer that, collectively, are configured to transport fluid in an amount of about 15 mL/min to about 150 mL/min through said plurality of channels in the first micropatterned polymer layer.

Topographic Features of Channels

Channels may contain three-dimensional structures to, for example, induce fluid mixing, or achieve other performance properties. Structures that induce fluid mixing can include topographic features directing fluid out of line with the flow direction (such as cross-hatched patterns or ridges placed diagonal to the flow), flexible elements that deform under the flow to create temporal perturbations in the fluid, and elements that induce rotational flows within the flow stream. Accordingly, in certain embodiments, a channel further comprises a mixing element to induce fluid mixing. In certain other embodiments, a channel comprises one or more changes in height or width of the chamber along the longitudinal axis of the chamber.

Another feature of the channels relates to two-dimensional structures, such as, networks of branched or bifurcated channels. The networks may feature smooth bifurcations and/or gradual changes in the cross-sectional channel dimensions, and may mimic the physiological properties of in-vivo vascular and/or micro-vascular networks. In some embodiments, the channels are formed by patterns of posts, instead of branched channels. For example, the post may be arranged at the vertices of a square lattice, leaving a latticework of channels in between. In certain embodiments, channels in the first micropatterned polymer layer form a biomimetic microvascular network, wherein each of the channels in the network have one of the heights/widths/length ranges specified above. For example, in certain embodiments, channels in the first micropatterned polymer layer form a biomimetic microvascular network comprising microchannels with a height not exceeding 50 µm. In yet other embodiments, the biomimetic microvascular network comprises an arrangement of polymer posts defining microchannels therebetween.

In certain embodiments, the first micropatterned polymer layer comprises a network of channels modeled as a "parking garage" structure with posts in a flat chamber. Microfluidic fabrication techniques are capable of producing such microvascular network architectures with extremely thin membranes, shallow channels, and posts or other supporting structures spaced across the blood flow chamber. An illustration of a post pattern architecture in a microvascular channel architecture constructed of polydimethylsiloxane is provided in FIG. 2. In other embodiments, the microvascular network layer defines bifurcated networks of microchannels. Such "parking garage" structures are contemplated to be amendable for use with extremely thin membranes (on the order of 1 µm) separating the vasculature network for blood flow from the gas flow channels (which mimic the alveolar air spaces in human lungs).

Modifications to the Surface of Channels

The inner surface of channels can be modified to achieve certain performance properties, such as improved resistance to degradation caused by a particular substance that may be present in the blood or gas, or reduce the risk that the channel may cause a transformation (e.g., inducement of blood clotting) of certain components in the blood. The surface modification may be a partial coating of the inner wall of the channel with a particular substance or a complete coating of the inner wall of the channel with a particular substance. Surface modifications that alter blood-material interactions can include surface-tethered compounds that reduce clotting (such as heparin), hydrophobic/hydrophilic monolayers that control protein adsorption to the device, degradable coatings that reduce build-up of adsorbed species in the device, and energetic treatments (such as energetic oxygen plasma) that alter surface chemistry and subsequent hydrophobicity/hydrophilicity. In certain embodiments, channels in the first micropatterned polymer layer are coated with a biological molecule, such as serum albumin or a surface protein that can be found in vasculature. In certain embodiments, channels in the first micropatterned polymer layer (particularly when the channels form a microvascular network) are coated with an anti-coagulant (such as heparin), which is contemplated to reduce blood clotting.

Thickness of the First Micropatterned Polymer Layer

The thickness of the first micropatterned polymer layer can be adjusted to optimize the performance properties of the device. For example, in embodiments where a third micropatterned polymer layer containing gas flow channels is bonded to the first micropatterned polymer layer, it is desirable for the thickness of the first micropatterned polymer layer to permit gas transfer between blood in the channels of the first micropatterned polymer layer and gas flow channels in the third micropatterned polymer layer. Accordingly, in certain embodiments, the first micropatterned polymer layer has a thickness of less than about 500 µm, less than about 300 µm, less than about 200 µm, less than about 150 µm, or less than about 100 µm. In certain other embodiments, the first micropatterned polymer layer has a thickness of less than about 150 µm. In yet other embodiments, the first micropatterned polymer layer and the second micropatterned polymer layer each independently have a thickness of less than about 150 µm. In still other embodiments, the first micropatterned polymer layer has a thickness of about 90 µm to about 150 µm, the second micropatterned polymer layer has a thickness of about 90 µm to about 200 µm, and channels in the first micropatterned polymer layer (i.e., channels forming the microvascular network) have a height of about 40 µm to about 60 µm.

Number of Channels in Each Micropatterned Polymer Layer

The number of channels in the first micropatterned polymer layer(s) may be selected according to desirable performance characteristics, such as the quantity of oxygen transfer or total blood flow, required for a particular application. Accordingly, in certain embodiments, each first micropatterned polymer layer comprises at least about 10 channels for blood flow, at least about 25 channels for blood flow, at least about 50 channels for blood flow, at least about 100 channels for blood flow, or at least about 500 channels for blood flow. Alternatively, in certain other embodiments, each first micropatterned polymer layer comprises from about 10 to about 50 channels for blood flow, about 20 to about 100 channels for blood flow, or about from about 100 to about 500 channels for blood flow.

Because the oxygenator device may contain multiple bi-layers, it is contemplated that the overall number of channels in the various first micropatterned layers may be greater than 1000, 2000, 3000, 5000, or 7000.

B. Features of the Second Micropatterned Polymer Layer

The second micropatterned polymer layer is positioned on the opposite side of the gas-permeable membrane from the first micropatterned polymer layer. Channels in the second micropatterned polymer layer may have the same or different height and width features compared to channels in the first micropatterned polymer layer.

In certain embodiments, channels in the second micropatterned polymer layer may be an exact mirror image of channels in the first micropatterned polymer layer and located precisely thereover, or may instead take another suitable form (e.g., a single channel coextensive with and located opposite the network of channels in the first micropatterned polymer layer across the membrane). Preferably, any walls in the second micropatterned polymer layer are aligned with a support feature in the first micropatterned polymer layer (i.e., walls in the second micropatterned polymer layer are not aligned over a channel in the first micropatterned polymer layer).

Channels in the second micropatterned polymer layer may contain a polymer post to provide additional structural support to the channel. Accordingly, in certain embodiments, at least one channel in the second micropatterned polymer layer comprises an arrangement of polymer posts. The polymer posts may be positioned so that they align with a support feature in the first micropatterned polymer layer.

In certain embodiments, a channel in the second micropatterned polymer layer is wide enough to cover a single channel in the first micropatterned polymer layer. In certain other embodiments, a channel in the second micropatterned polymer layer wide enough to cover more than one channel in the first micropatterned polymer layer, such as it covers 2, 3, 4, 10, or 15 channels in the first micropatterned polymer layer. In certain other embodiments, at least one channel in the second micropatterned polymer layer has a width spanning at least 10 channels in the microvascular network of the first micropatterned polymer layer. In certain embodiments, at least one channel in the second micropatterned polymer layer is in gas communication with at least ten channels in the first micropatterned polymer layer via the gas-permeable membrane.

In certain embodiments, channels in the second micropatterned polymer layer have a height in the range of about 20 μm to about 150 μm, about 30 μm to about 120 μm, or about 40 μm to about 110 μm. In certain embodiments, channels in the second micropatterned polymer layer have a width in the range of about 50 μm to about 1.5 mm, about 100 μm to about 500 μm, or about 50 μm to about 1 mm. In certain embodiments, channels in the second micropatterned polymer layer have a length in the range of about 0.005 cm to about 3 cm, about 0.1 cm to about 1.5 cm, about 0.5 cm to about 1.0 cm, about 0.5 cm to about 0.8 cm, or about 0.7 cm.

In certain embodiments, the thickness of the second micropatterned polymer layer is the same or different than the thickness of the first micropatterned polymer layer. For example, in certain embodiments, the second micropatterned polymer layer has a thickness of less than about 500 μm, less than about 300 μm, less than about 200 μm, less than about 150 μm, or less than about 100 μm.

Channels in the second micropatterned polymer layer may have cross-sections that are rectangular, triangular, round, or other geometries. In certain embodiments, channels in the second micropatterned polymer layer have cross-sections that are rectangular. In certain embodiments, channels in the second micropatterned polymer layer are hemispherical or rounded.

Channels in the second micropatterned polymer layer can be molded in a polymeric material such as polystyrene, polycarbonate, polydimethylsiloxane, polymethylmethacrylate, cyclic olefin copolymer (e.g., ZEONOR), polysulfone, or polyurethane. For certain applications, the use of biodegradable or biocompatible materials, such as polyglycerol sebacate, polyoctanediol citrate, polydiol citrate, silk fibroin, polyesteramide, and/or polycaprolactone may be advantageous. In certain embodiments, the second micropatterned polymer layer is made from a gas-permeable polymer.

In certain embodiments, the second micropatterned polymer layer is made of a gas-permeable silicone. In certain embodiments, the second micropatterned polymer layer is made of phenyl vinyl methyl siloxane, vinyl methyl siloxane, or fluorosilicone. In certain embodiments, the second micropatterned polymer layer is made of the silicone material Cosmesil K10 (produced by Cosmedica Ltd, Cardiff, United Kingdom) or the silicone material MDX4-4210 (produced by Dow Corning Corporation, Midland, Mich., as a mixture containing 55.0-75.0 wt % dimethylvinyl-terminated dimethylsiloxane and 15.0-35 wt % trimethylated silica). In certain embodiments, second micropatterned polymer layer is made of polydimethylsiloxane.

The material used to make the first micropatterned polymer layer may be the same or different than the material used to make the second micropatterned polymer layer. In certain embodiments, the first micropatterned polymer layer and the second micropatterned polymer layer are each made of polydimethylsiloxane.

C. Optional Third Micropatterned Polymer Layer

Devices herein may optionally comprise a third micropatterned polymer layer attached to either the first micropatterned polymer layer or the second micropatterned polymer layer. The third micropatterned polymer layer contains channels, e.g., channels for gas flow. One objective for the third micropatterned polymer layer is to increase gas permeation to blood in channels of the first micropatterned polymer layer. Thus, one embodiment provides a device comprising a third micropatterned polymer layer defining at least one channel for gas supply, wherein said third micropatterned polymer layer is attached to the surface of the first micropatterned polymer layer located opposite the surface attached to the gas-permeable polymer membrane. The first micropatterned polymer layer and the third micropatterned polymer layer used in such embodiments are preferably made from materials that are permeable to gas, particularly oxygen and carbon dioxide. In certain embodiments, the third micropatterned polymer is made from one of the materials described above for the first micropatterned polymer layer. In certain embodiments, the third micropatterned polymer layer is made from the same material as the first micropatterned polymer layer.

It is contemplated that increasing the number of channels for gas flow in proximity to channels for blood flow can increase the rate at which gas is transferred to the fluid. Accordingly, reducing the thickness of gas permeable material separating a channel for gas flow from a channel for blood flow is contemplated to increase the rate at which gas is transferred to the blood. Thus, in certain embodiments, the thickness of gas permeable material separating any channel for gas flow from an adjacent channel for blood flow is about 25 μm to about 200 μm. In certain embodiments, the thickness of gas permeable material separating any channel for gas flow from an adjacent channel for blood flow is about 20 μm to about 100 μm. The number of channels for gas flow in the third micropatterned polymer layer may be greater than 5, 10, 20, 50, 100, 500, or 1000.

In certain embodiments, the device further comprises a third micropatterned polymer layer defining at least one channel for gas supply, wherein said third micropatterned polymer layer is attached to the surface of the first micropatterned polymer layer located opposite the surface attached to the gas-permeable polymer membrane, the first micropatterned polymer layer has a thickness of about 90 μm to about 150 μm, channels in the first micropatterned polymer layer (i.e., channels forming the microvascular network) have a height of about 40 μm to about 60 μm, the second micropatterned polymer layer has a thickness of about 90 μm to about 200 μm; and each of the first micropatterned polymer layer, the second micropatterned polymer layer, and the third micropatterned polymer layer are made of polydimethylsiloxane.

In embodiments where the device comprises a third micropatterned polymer layer defining at least one channel for gas supply attached to the surface of the first micropatterned polymer layer located opposite the surface attached to the gas-permeable polymer membrane, the first micropatterned polymer layer may comprise hollow posts that connect channels for gas supply in the second micropatterned polymer layer with channels for gas supply in the third micropatterned polymer layer. For example, the post in the first micropatterned polymer layer may be arranged at the vertices of a square lattice, leaving a latticework of channels in between. One contemplated benefit of the hollow posts is that oxygen may penetrate through the hollow post into channels in the first micropatterned polymer layer.

D. Features of the Gas-Permeable Membrane

The gas-permeable membrane is selected to achieve rapid transfer of gas (e.g., oxygen and carbon dioxide), while providing sufficient durability to prevent rupture, such as rupture due to forces applied to the membrane by blood flow through the device. The gas-permeable membrane desirably does not permit any significant amount of fluid (e.g., blood proteins or water) to pass from channels in the first micropatterned polymer layer to gas flow channels in the second micropatterned polymer layer.

The chemical composition and thickness of the gas-permeable membrane impact the performance properties of the gas-permeable membrane. Accordingly, in certain embodiments, the gas-permeable membrane has a thickness of no more than 150 μm. In certain other embodiments, the gas-permeable membrane has a thickness of no more than 120 μm, 100 μm, 80 μm, 60 μm, 40 μm, 30 μm, 20 μm, or 10 μm. In certain other embodiments, the gas-permeable membrane has a thickness of no more than 10 μm. In certain other embodiments, the gas-permeable membrane has a thickness of about 10 μm to about 150 μm, about 10 μm to about 100 μm, about 30 μm to about 100 μm, about 30 μm to about 60 μm, about 10 μm to about 40 μm, about 10 μm to about 30 μm, or about 10 μm to about 20 μm. In certain other embodiments, the gas-permeable membrane has a thickness of about 10 μm to about 30 μm. In certain other embodiments, the gas-permeable membrane has a thickness of about 25 μm to about 35 μm. In certain other embodiments, the gas-permeable membrane is made from PDMS and has a thickness of 45.37 μm, 23.81 μm, 17.69 μm, 11.51 μm, or 9.127 μm.

The chemical composition and thickness of the gas-permeable membrane can also be characterized according to oxygen gas permeance. Accordingly, in certain embodiments, the gas-permeable membrane has an oxygen gas permeance (which depends upon its bulk permeability and the membrane thickness) of at least $1 \times 10^{-6}$ mL/s/cm$^2$/cm Hg. In certain other embodiments, the gas-permeable membrane has an oxygen gas permeance of at least $1 \times 10^{-5}$ mL/s/cm$^2$/cm Hg, $3 \times 10^{-5}$ mL/s/cm$^2$/cm Hg, $7 \times 10^{-5}$ mL/s/cm$^2$/cm Hg, or $1 \times 10^{-4}$ mL/s/cm$^2$/cm Hg.

Further, the chemical composition and thickness of the gas-permeable membrane can also be characterized according to carbon dioxide gas permeance. Accordingly, in certain embodiments, the gas-permeable membrane has a carbon dioxide gas permeance of at least $1 \times 10^{-6}$ mL/s/cm$^2$/cm Hg. In certain embodiments, the gas-permeable membrane has a carbon dioxide gas permeance of at least $1 \times 10^{-5}$ mL/s/cm$^2$/cm Hg, $2 \times 10^{-5}$ mL/s/cm$^2$/cm Hg, or $5 \times 10^{-5}$ mL/s/cm$^2$/cm Hg.

The gas-permeable membrane is preferably made of a material that is gas-permeable, non-porous, has hemocompatibility (such as membrane materials used in ECMO devices) is compatible with the manufacturing procedures described herein, and is compatible with covalently-linked biological molecules. Exemplary materials for use in making the gas-permeable membrane include PolyDiMethylSiloxane (PDMS), polyethersulfone, polycarbonate, polyimide, silicon, cellulose, PolyMethylMethacrylate (PMMA), PolySulfone (PS), PolyCarbonate (PC), or from a degradable material such as PLGA, PolyCaproLactone (PCL) or Biorubber]. In certain embodiments, the gas-permeable polymer membrane is made of polydimethylsiloxane.

II. PERFORMANCE ATTRIBUTES OF THE OXYGENATOR DEVICE

The amount of gas transferred to blood flowing through the oxygenator device can be increased by increasing the number of bi-layers (where each bi-layer contains a first micropatterned polymer layer, a second micropatterned polymer layer, and a gas-permeable membrane) in the device. For example, in certain embodiments, device comprises from about 5 to about 50 bi-layer structures arranged in a stack. In certain embodiments, device comprises from about 5 to about 100 bi-layer structures arranged in a stack, or the device comprises from about 50 to about 100 bi-layer structures arranged in a stack. The multiple bi-layers may be bonded together using chemical (e.g., oxygen plasma bonding) or mechanical techniques.

One benefit of the extracorporeal membrane oxygenator devices described herein is that they require only a minimal volume of blood to prime the device. For example, in certain embodiments, the device is adapted to have a blood prime volume not exceeding 10 mL. In certain other embodiments, the device is adapted to have a blood prime volume not exceeding 5 mL, 10 mL, 20 mL, or 50 mL. In certain other embodiments, the device has a blood prime volume of about 50 mL when configured to permit blood flow at a rate of 1 L/min.

In certain embodiments, the device is adapted to transfer oxygen between the microvascular network in the first micropatterned polymer layers and the gas-supply channels of the second micropatterned polymer layers at a rate of at least 4 mL/min. In yet other embodiments, the device is adapted to transfer oxygen between the microvascular network of the first micropatterned polymer layers and the gas-supply channels of the second micropatterned polymer layers at a rate of at least 4 mL/min when blood is passed through the device at a rate of about 100 mL/min. In yet other embodiments, the device is adapted to transfer oxygen between the microvascular network of the first micropatterned polymer layers and the gas-supply channels of the second micropatterned polymer layers at a rate of about 4 mL/min to about 6 mL/min when blood is passed through the device at a rate of about 100 mL/min. In yet other embodiments, the device is adapted to transfer oxygen between the microvascular network of the first micropatterned polymer layers and the gas-supply channels of the second micropatterned polymer layers at a rate of about 5 mL/min when blood is passed through the device at a rate of about 100 mL/min.

Devices described herein can be used to transfer different types of gas to blood. In certain embodiments, the gas comprises oxygen. In certain embodiments, the gas is air, or air that has been enriched in oxygen content (such as air having an oxygen content of greater than 25%, greater than 35%, or greater than 50%). Further, in certain embodiments, channels in the first micropatterned polymer layer form a microvascular network for blood flow which comprises blood, and the channels for gas supply comprise oxygen.

III. DISTRIBUTION SYSTEM FOR DELIVERING FLUID AND GAS TO THE OXYGENATOR DEVICE

The oxygenator device may comprise a distribution system for delivering gas to channels in the second micropatterned polymer layer, and delivering blood to channels in the first micropatterned polymer layer (e.g., the microvascular network formed by channels in the first micropatterned polymer layer). The distribution system may comprise branching or bifurcating microchannels, biomimetic vascular-like channels, or a manifold structure. Controllable access to the channels may be provided by vascular-like channel structures, structures that provide a smooth path for fluid flow, or other configurations.

Figure 3:
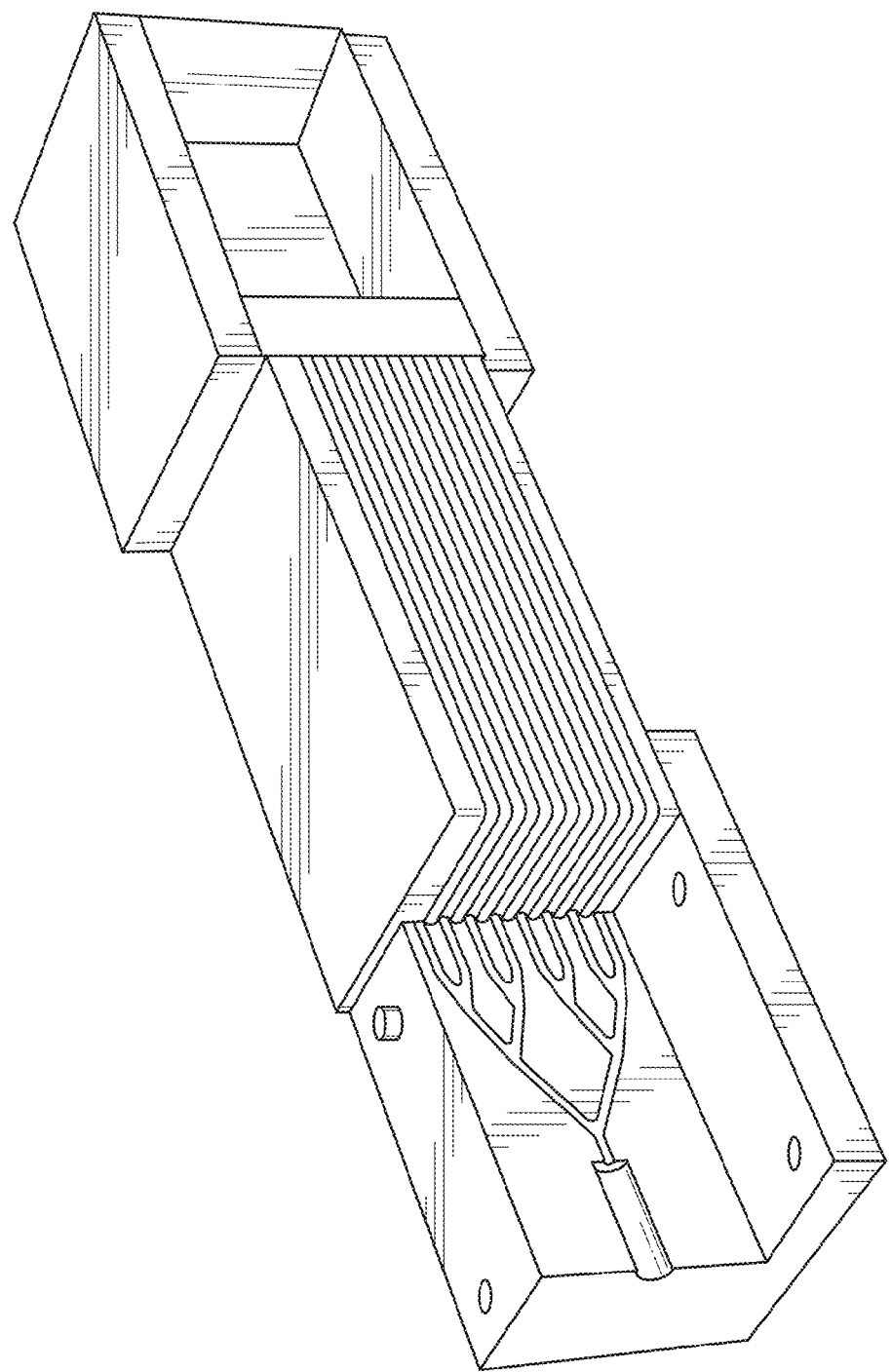
FIG. 3 is an illustration of an oxygenator device containing a fluid distribution manifold that minimizes the fluid volume and efficiently and smoothly distributes fluid to multiple layers in a device.

In certain embodiments, a distribution manifold is used that minimizes the fluid volume contained therein during operation. This serves to reduce the blood prime volume of the assembled oxygenator device. In conventional oxygenation devices, the blood prime volume is principally determined by the fluid distribution network and other auxiliary components (such as, e.g., pumps, heat exchangers, measuring devices, and long sections of tubing with interconnects), rather than by the oxygenator itself. In various embodiments of the present invention, the contribution of the auxiliary components is significantly reduced by integrating a low-fluid-volume distribution manifold with the oxygenator as part of the overall device implementation. An illustration of a fluid distribution manifold that minimizes the fluid volume and efficiently and smoothly distributes fluid to multiple layers in an oxygenator device is provided in FIG. 3. Processes for fabricating such a device include solid freeform fabrication methods (e.g., stereolithography, fused deposition modeling, three-dimensional printing, etc.), as well as molding or embossing techniques from machined masters in which the manifold is assembled by stacking thin films of similar or dissimilar patterns, which results in a 3D distribution network.

Accordingly, in certain embodiments, the oxygenator device further comprises means for delivering gas to channels in the second micropatterned polymer layer and blood to channels in the first micropatterned polymer layer.

In yet other embodiments, the device further comprises a low-fluid-volume distribution manifold fluidically coupling the microvascular networks of the first polymer micropatterned polymer layers to one another.

In yet other embodiments, microvascular networks of the first micropatterned polymer layers are fluidically connected with each other via a first through hole through the stack, and the channels of the second micropatterned polymer layers are fluidically connected with each other via a second through hole through the stack.

IV. FLUID CONDUITS AND PUMPS

The oxygenator devices described herein may optionally contain one or more of: (i) a first access conduit affording fluid communication with an input end of one or more channels in the first micropatterned polymer layer; (ii) a first return conduit affording fluid communication with an output end of one or more channels in the first micropatterned polymer layer; (iii) a first pump for ensuring that a fluid entering the first access conduit flows through one or more channels in the first micropatterned polymer layer and out the first return conduit, (iv) a first access conduit affording fluid communication with an input end of one or more channels in the second micropatterned polymer layer; and (vi) a second pump for ensuring that a gas entering the first access conduit flows through one or more channels in the second micropatterned polymer layer.

Access and return conduits can convey blood to and from channels in the first micropatterned polymer layer. In certain embodiments, the oxygenator device is connected to the vasculature of a patient. Access to the patient's vasculature may be through an IV needle, cannulae, fistula, catheter, or an implanted access device. The access points may be existing points for previous treatments and may be arterio-venous or veno-venous in nature. The conduits can be standard medical tube materials including polymers such as silicone rubber, polyurethane, polyethylene, polyvinyl chloride, and latex rubber. An approximate size range of the inner diameter of the access conduits can be 300 μm-1 cm. The access conduits can be integrated into the oxygenator device, or can instead be separate and have attachment points to connect to the oxygenator device.

A pump may regulate blood flow rate into the device, e.g., if arterial blood pressure is not high enough for the particular application or if a venous-venous access is deemed more desirable. In some cases, a physiological blood pressure of 120 mmHg may be sufficient to drive blood flow from an arterial access through the oxygenator device and back to the patient. In other cases, particularly where veno-venous access is used, a pump is used to drive blood through the oxygenator device.

V. RESERVOIR FOR GAS STORAGE

The oxygenator device may optionally comprise a reservoir for gas storage. In certain embodiments, the reservoir is an extension of at least one channel in the second micropatterned polymer layer. In certain embodiments, the reservoir contains oxygen. In certain embodiments, the reservoir contains air.

VI. GASES FOR USE WITH THE OXYGENATOR DEVICES

The oxygenator devices described herein are contemplated to be amenable for use with a wide variety of gases. For example, in certain embodiments, the gas is oxygen, carbon dioxide, air, nitrogen, or an inert gas. In certain embodiments, channels in the first micropatterned polymer layer comprise blood, and channels in the second micropatterned polymer layer comprise oxygen. In certain embodiments, cellular components are temporarily removed from the blood before the blood is passed through the oxygenator device, then the cellular components are reintroduced to the blood that has passed through the oxygenator device—this is contemplated to reduce the potential for blood coagulation within the oxygenator device.

VII. METHODS FOR TRANSFERRING GAS TO BLOOD

The devices described herein are useful for transferring a gas to blood. Accordingly, one aspect of the invention provides a method for transferring a gas to blood. The method comprises passing blood through a device described herein having a gas in at least one channel for gas flow, to thereby transfer said gas to the blood. In certain embodiments, the gas comprises oxygen (such as where the gas is air, or air enriched with oxygen).

The rate at which blood is passed through the device can impact the performance properties of the device. Accordingly, in certain embodiments, blood is passed through the device at a rate of about 50 mL/min to about 120 mL/min, or about 120 mL/min to about 500 mL/min, about 400 mL/min to about 600 mL/min, about 500 mL/min to about 1 L/min, about 1 L/min to about 2 L/min, about 2 L/min to about 3 L/min, about 3 L/min to about 4 L/min, or about 400 mL/min to about 4 L/min. In certain embodiments, blood is passed through the device at a rate of about 400 mL/min to about 4 L/min. In certain embodiments, the method is characterized in that oxygen is transferred to blood at a rate of about 5 mL/min when blood is passed through the device at a rate of about 100 mL/min. In certain embodiments, the device is fluidly connected to the blood vasculature of a patient. In certain embodiments, the method further comprises transferring a gas dissolved in said blood to a channel for gas flow in the device.

VIII. PREPARATION OF OXYGENATOR DEVICES

Oxygenator devices can be prepared by bonding a first micropatterned polymer layer to a thin, gas-permeable membrane, which is bonded to a second micropatterned polymer layer. The first micropatterned polymer layer and second micropatterned polymer layer can be prepared using standard microfabrication methods, which are described below. Detailed procedures for preparing the thin, gas-permeable membrane and bonding the membrane to the first micropatterned polymer layer and the second micropatterned polymer layer are also described below.

More particularly, in embodiments where the first micropatterned polymer layer contains channels in the form of a microvascular network and the second micropatterned polymer layer contains channels for oxygen-supply, such layers can be manufactured using a variety of microfabrication techniques, such as photolithographic patterning and replica molding. The thin gas-permeable membrane may be manufactured by spin-coating a liquid prepolymer mixture onto a silicon wafer, e.g., at a speed between 500 and 6000 revolutions per minute (rpm). The mixture may include a solvent that reduces the viscosity, thus enabling smaller membrane thicknesses (e.g., thicknesses of less than one fourth of those achievable without the solvent). To assemble the bi-layer structure, the gas-permeable membrane may be bonded to one of the polymer layers by sandwiching it between that polymer layer and the silicon wafer while the gas-permeable membrane is still in a liquid-like state, and then curing the silicon-membrane-polymer structure in an oven. Thereafter, the membrane-polymer construct may be released from the silicon wafer (e.g., by peeling it off the wafer, or by inducing the degradation of a sacrificial layer between the wafer and the membrane), and the second polymer layer may be bonded to the free side of the membrane. Alternatively, the gas-permeable membrane may be bonded to each of the polymer layers using plasma-bonding. In another embodiment, an integrated structure including the gas-permeable membrane and one of the polymer layers may be manufactured by spin-coating a prepolymer mixture onto a micropatterned silicon wafer with recesses that are complementary to the channel structure of the polymer layer so as to fill the recesses and form a thin, continuous polymer layer thereover. Multiple bi-layer structures may be connected by, e.g., plasma-bonding.

A. General Microfabrication Methods

Figure 4:
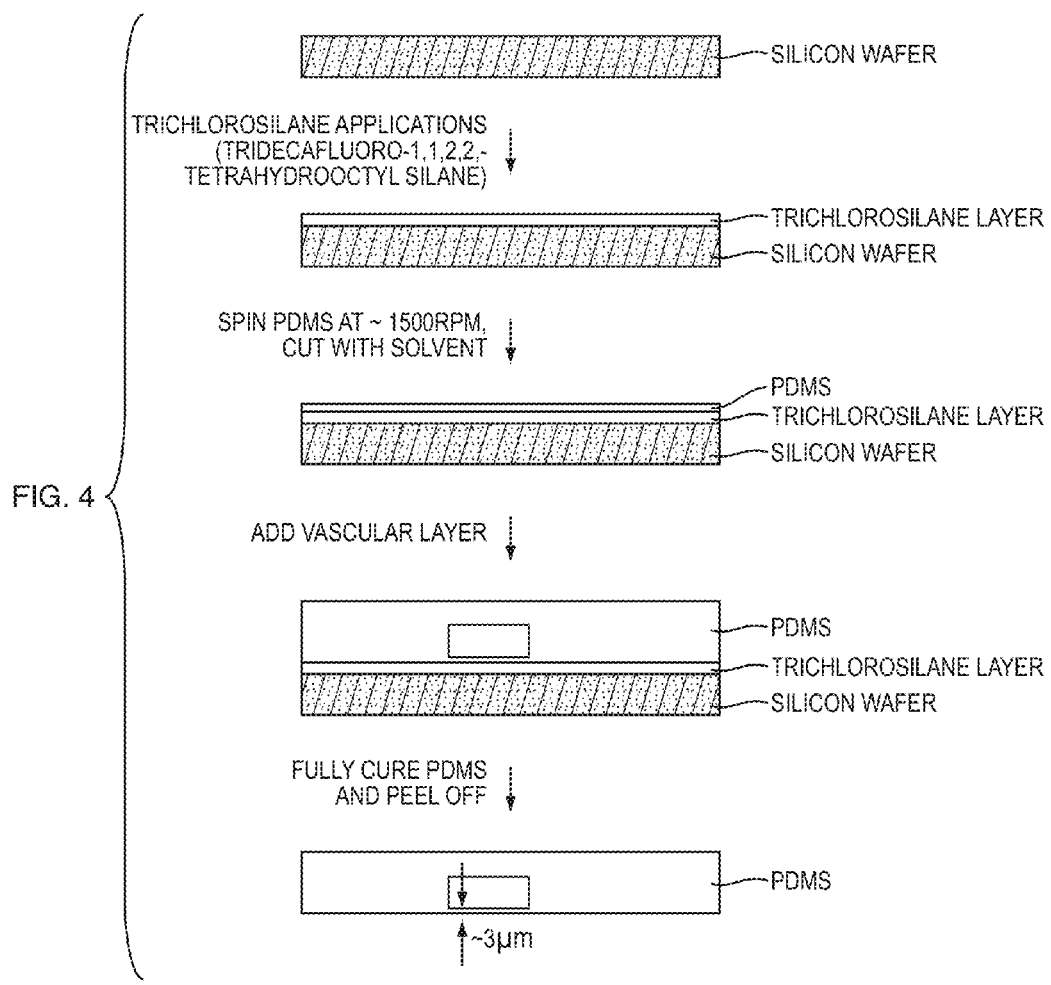
FIG. 4 depicts a procedure for spin-coating polydimethylsiloxane onto a mold.

The first micropatterned polymer layer and the second micropatterned polymer layer can be prepared where a polymer is molded to a microfabricated mold. For example, polydimethylsiloxane (PDMS) may be spin-coated onto the mold, as shown in FIG. 4. However, other gas permeable polymers may be employed as well, including other organo-silicone materials (e.g., polysiloxane, PDMS variants such as MDX-4, and modified PDMS compositions that enhance gas (e.g., oxygen and carbon dioxide) permeability), polyethylene, and polyurethane-like materials.

The mold used above may be created through microfabrication, typically photopatterned photoresist; however, etched silicon, cured epoxy, and/or electroformed metal can also be used. Prepolymer is then poured into the mold, and the mold is spun at a specific speed to create a thin layer of the prepolymer. The prepolymer is then cured, and the device released from the mold after curing.

An alternative method to create a polymer layer with channels is to apply pressure to the prepolymer in the mold from above using a second microfabricated mold. This replaces the spin coating step, and the device is cured and then released from the mold.

B. Methods for Preparing a Thin, Gas-Permeable Membrane and Bonding it to the First Micropatterned Polymer Layer and Second Micropatterned Polymer Layer Thin polymer membranes, primarily of PDMS, have been used in a variety of applications such as pressure-driven adjustable lenses and surfaces with variable hydrophobicity. PDMS has a high oxygen diffusivity; accordingly, a thin PDMS membrane can allow sufficient oxygen and other gases to diffuse from a blood flow channel to an oxygen flow channel. Although the ensuing discussion focuses on creating thin polymer membranes using PDMS, the same processes can be used to create thin membranes from other polymers.

Fabricating Thin Polymer Membranes

In general, the process is based on using a silicon wafer spinner to spin down the polymer to a thin layer. In certain embodiments, a solvent may be used to reduce the viscosity of the polymer, allowing it to be thinned down even further. Different approaches may be employed to spinning polymers down to thin membranes.

In one exemplary approach, a very thin layer of uncured PDMS is spun onto a treated silicon wafer at about 500 RPM, 100 R/S for approximately 60 seconds. The PDMS membrane is cured on the wafer at about 60° C. for approximately one hour. The edges are released with a square razor, and the membrane is peeled off the wafer and stored between blue wax paper circles. The membrane may then be sandwiched between and attached to two micropatterned polymer layers using, e.g., plasma-bonding techniques.

Figure 5:
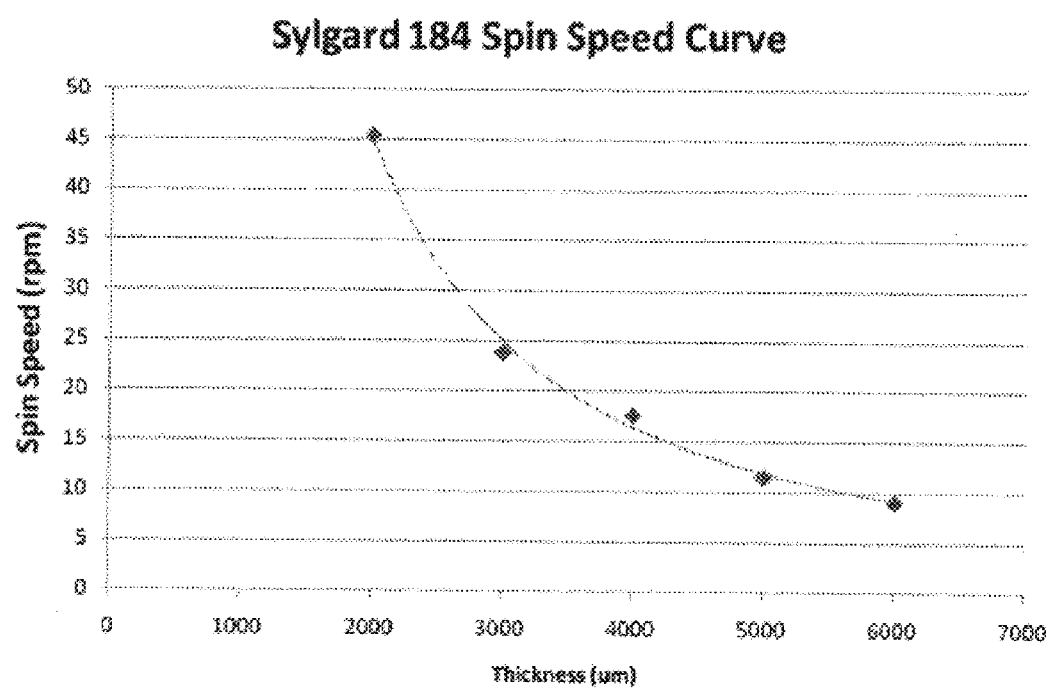
FIG. 5 is a graph showing thickness of a polydimethylsiloxane layer as a function of spin speed.

In another exemplary approach, illustrated in FIG. 4, a PDMS prepolymer and curing agent are mixed in a 10:1 ratio, and the mixture is let sit in a vacuum to remove air bubbles. A blank silicon wafer (i.e., a wafer without any geometries patterned into it) is placed on the spinner, and approximately 15-20 grams of polymer are poured on its center. The polymer is spun down at a speed between 500 and 6000 rpm for about 60 s with a ramp-up speed of about 500 rpm/s. This creates a uniformly thin polymer layer, whose thickness depends on the spin speed, as shown in FIG. 5 in a PDMS spin curve. Thus, the desired thickness may be achieved by adjusting the spin speed.

The membrane is then combined with a polymer layer that carries the geometries of interest, such as capillaries, cell-holding chambers, or other microfluidic channels (and which may have been fabricated beforehand). The polymer layer is attached to the thin polymer membrane with the empty space of the geometries facing the membrane. This step is performed immediately after the polymer has been spun and is still in its liquid state to maximize the strength of the bond between the two. The sandwich structure formed by the silicon wafer, thin membrane, and polymer layer is then transferred to a hot oven (kept, for example, between 60 and 85° C.). After being in the oven for about an hour, the thin polymer membrane has usually completely cured, forming a particularly strong bond that attaches the membrane to the roof of the microfluidic geometries. The membrane/polymer-layer structure may then be peeled off the silicon wafer. This can be done either by pulling the layer and separating it from the wafer, or by using one of the release mechanisms described below.

Figure 6:
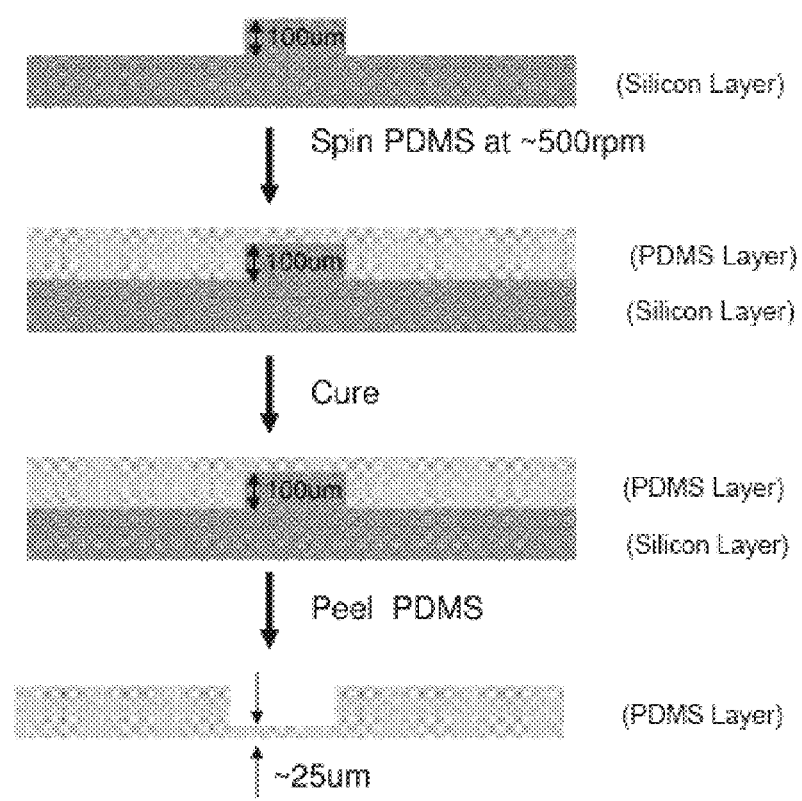
FIG. 6 depicts a procedure where a thin polymer membrane is coated onto a silicon wafer with raised and recessed features, which functions as a mold.

In yet another exemplary approach, illustrated in FIG. 6, the thin polymer membrane is coated onto a silicon wafer with raised and recessed features, which functions as a mold. The wafer is positioned on the spinner, polymer is mixed, and 15-20 g of polymer are applied to the center of the wafer. The wafer is then spun at a speed between about 100 rpm and about 7000 rpm to produce a layer as thick as the tallest features of the silicon mold, plus the desired thickness of the membrane. The polymer is cured in an oven and separated from the silicon wafer as described before. A (thicker) polymer layer may then be bonded to the patterned layer to cap the channels.

Use of Solvents to Reduce Membrane Thickness

The smallest thickness of the polymer membrane achievable by spinning is limited by the viscosity of PDMS (or any other polymer). Increasing the amount of curing agent from a ratio of 10:1 to 10:2 helps slightly.

In applications requiring particularly thin (e.g., submicron) layers, the polymer may be mixed with a solvent. This temporarily reduces the viscosity of the mixture, allowing it to be spun into a thinner layer. Moreover, the low boiling point of the solvent causes the solvent to evaporate in the curing step. Evaporation is further facilitated by the minimal thickness of the membrane, which constitutes the diffusion length the solvent molecules have to traverse in the polymer before coming in contact with air.

Solvents that may be used in combination with PDMS include diisopropylamine, triethylamine, pentane, chloroform, ether, tetrahydrofuran (THF), hexanes, trichloroethylene, n-heptane, cyclohexane, dimethoxyethane (DME), benzene, chlorobenzene, methylene chloride, t-butyl alcohol, 2-butanone, ethyl acetate, dioxane, 1-propanol, acetone, pyridine, ethyl alcohol, Dow OS-20 (methyl-siloxane), 200 fluid (Polydimethylsiloxane), Amtex RC21, xylene and toluene. Various considerations relevant to the selection of a solvent, including its ability to swell PDMS, its boiling point, and health hazards may be considered as reported in the literature. The spin curve of native PDMS reaches an asymptote of approximately 30 μm, and the spin curve of 10:2 PDMS reaches an asymptote of 25 μm, at 2500 rpm. However, the thickness of PDMS cut with toluene can reach submicron levels in a toluene to PDMS ratio of 4 to 1 or higher, at 1500 rpm. See, for example, Hongkai et al. in *Lab on a Chip* (2005) vol. 5, 1393-1398.

Release Mechanisms

Besides simple release of the polymer membrane from the silicon wafer by slowly pulling it loose, various release mechanisms may be used to facilitate the process and ensure that the thin membrane does not tear. These mechanisms rely either on applying an anti-stick coating to the silicon wafer that prevents PDMS from sticking, or on spinning a thin sacrificial layer on the silicon wafer before applying the polymer.

One way to make silicon less adhesive to PDMS is to coat it with TEFLON (tridecafluoro-1,1,2,2,-tetrahydrooctyl silane). This may be accomplished in an inductively coupled plasma (ICP) etcher with a one-cycle short recipe limited to the TEFLON deposition part of the cycle (and not the etching step). Another way of reducing the adhesion of PDMS to silicon involves coating the silicon surface with a thin layer of photoresist, such as Shipley 1822, at 4000 rpm.

A sacrificial layer of, for example, photoresist, sucrose, or UV-degradable PDMS may be spun onto the silicon wafer before the polymer is applied. The polymer is spun down to the desired thickness, attached to the layer with the microfluidic geometries if necessary, and then cured. Then, degrading of the sacrificial layer may be induced, either by exposure to UV light (in the case of the photoresist and the UV-degradable PDMS), or by letting the coated wafer sit overnight in a water bath (in the case of sucrose). This causes the polymer layer to release from the silicon wafer without the need to pull the two apart, thus reducing the possibility of membrane rupture.

Intubation of Layers and Device Assembly

To prepare the layers for integration into a microfluidic network, they may be intubated. For that purpose, the patterned side of the vascular layer may be covered with tape. Then, inlet and outlet holes may be punched out with a 2 mm biopsy punch. Four approximately four-inch long pieces of size 05 Silastic tubing may be cut, and, into each through-hole, a piece of tubing may be fed such that approximately a centimeter protrudes on the patterned side. The vascular layer may be placed on a spacer (such as a much smaller petri dish or a small PDMS base) and taped to the dish to secure it. The long ends of the tubes may be taped down to secure them and keep them away from glue. A small amount of uncured PDMS may be applied with a toothpick around the base of the tubing to glue it in place. The glue is then typically cured in the oven at 60° C. for approximately an hour (although less time may be sufficient in many embodiments). Then, the layer is removed from the oven. Excess tubing on the underside of the device may be trimmed off by tugging on it slightly to extend it, and clipping it off with a pair of nail clippers or a razor. The tugging ensures that the tube will be trimmed slightly above the bottom of the through hole and will not protrude during bonding. The process may be repeated with the oxygen-supply layer. In preferred embodiments, two tubes per layer are provided, one for inlet and one for outlet.

To assemble the two layers into a bi-layer structure, the tape is removed from the patterned sides of the vascular and oxygen-supply layers. The vascular layer may be plasma-bonded to the PDMS membrane at about 180 Watts for approximately 20 seconds, and then pressed to the membrane firmly so that the entireties of both bonding surfaces come into contact. The vascular-to-membrane bond is allowed to set for a few minutes, following which the oxygen-supply layer is plasma-bonded to the membrane with the same settings. Excess PDMS may be trimmed with scissors or a razor. A very small amount of uncured PDMS may be smeared with a toothpick around the perimeter of the device to seal its edges. A label may be adhered with a small dot of uncured PDMS. The device is then typically cured at about 60° C. for approximately an hour.

FIG. 7 is an illustration of devices fabricated using the techniques described above, where solid black rectangles denote channels.

C. Preferred Methods of Preparing a Bi-Layer Structure for Use in Extracorporeal Membrane Oxygenator Devices Another aspect of the invention provides a method of manufacturing a bi-layer structure for use in an extracorporeal membrane oxygenator device, the structure including first and second micropatterned polymer layers and a gas-permeable polymer membrane therebetween. The method comprises spin-coating a prepolymer mixture onto a silicon wafer so as to form the polymer membrane, the polymer membrane being attached to the silicon wafer at a first side of the polymer membrane; bonding the first micropatterned polymer layer to a second side of the polymer membrane; releasing the polymer membrane from the silicon wafer; and bonding the second micropatterned polymer layer to the first side of the polymer membrane.

In certain embodiments, the spin-coating is performed at a spinning speed between about 500 rpm and about 6000 rpm. In certain embodiments, the prepolymer mixture comprises a solvent that reduces a minimum achievable thickness of the layer by a factor of at least 4. In certain embodiments, releasing the polymer membrane comprises peeling the polymer membrane off the silicon wafer. In certain embodiments, releasing the polymer membrane comprises causing degradation of a sacrificial layer coated onto the silicon wafer before spin-coating of the prepolymer mixture onto the wafer. In certain embodiments, bonding the first micropatterned polymer layer to the polymer membrane comprises placing the first micropatterned polymer layer onto the second side of the polymer membrane before the membrane has cured, and exposing the combined structure to heat so as to simultaneously cure the polymer membrane and bond the polymer membrane to the first micropatterned polymer layer. In certain embodiments, bonding the first micropatterned polymer layer to the polymer membrane comprises plasma-bonding.

Another aspect of the invention provides a method of manufacturing a bi-layer structure for use in an extracorporeal membrane oxygenator device, the structure including first and second micropatterned polymer layers and a gas-permeable polymer membrane therebetween. The method comprises spin-coating a prepolymer mixture onto a micropatterned silicon wafer so as to fill recessed features of the micropatterned silicon wafer and form a thin, continuous polymer layer thereover, thereby forming an integrated structure including the first micropatterned polymer layer and the gas-permeable polymer membrane; releasing the integrated structure from the silicon wafer; and bonding the second micropatterned polymer layer to the exposed side of the gas-permeable polymer membrane.

IX. MEDICAL AND OTHER APPLICATIONS FOR OXYGENATOR DEVICES

Oxygenator devices described herein are contemplated to be useful in artificial lung applications, particularly, in medical device products for neonates with breathing and cardiac difficulties, surgical devices for cardiopulmonary bypass, and bridge devices for pediatric and adult patients awaiting lung transplants. In addition, patients with chronic lung diseases may be able to utilize longer-term devices of this nature, in order to support blood oxygenation. Further, the oxygenator devices described herein are contemplated to be useful as lung assist devices for patients with lung damage or adult respiratory distress syndrome (ARDS), treatment of chronic obstructive pulmonary disease, enhanced oxygenation or carbon dioxide removal for fire/blast victims, and eventual long-term partial or complete lung replacement, among others.

Benefits of oxygenator devices described herein include that they (i) are more physiologically realistic than conventional ECMO and artificial lung devices in terms of design, materials, and/or biocompatibility properties, (ii) are smaller than certain EMCO devices currently on the market, (iii) have higher-efficiency gas exchange than certain EMCO devices currently on the market, (iv) are capable of using ambient air may instead of a concentrated high-pressure oxygen source, (v) have superior biocompatibility, and (vi) are less susceptible to complications arising from anticoagulation therapy. The superior performance features of the oxygenator devices described herein derive, in part, from the high-precision bifurcated microchannel networks with precise architecture. The oxygenator devices are also compatible with biocompatible surface coatings (e.g., endothelial cell lining along the microchannel networks) that can reduce occurrences of inflammation and reduce the need for anticoagulative therapy.

Oxygenator devices described herein overcome various limitations of conventional ECMO devices by providing devices that are characterized by, e.g., biomimetic vascular network architectures, shallow channels with improved architecture for enhanced oxygen diffusivity, low-fluid volume distribution manifolds, and/or ultra-thin gas-permeable membranes. A preferred oxygenator device in accordance with the invention includes a stack of (between a few and hundreds of) bi-layer polymer structures, each of which is formed of two (typically distinct) micropatterned polymer layers bonded to each other by a gas-permeable membrane. One of the micropatterned polymer layers of the bi-layer structure defines a microvascular network, while the other layer defines channels for gas (e.g., air or oxygen) supply. In operation, blood flows through the microvascular network, which may be biomimetic, and takes up oxygen from the oxygen-supply channels across the membrane. To achieve high gas transfer, the device incorporates a very thin membrane (e.g., having a thickness of less than 50 µm, less than 10 µm, or even approaching 1 µm) and shallow microvascular channels (e.g., having a channel height not exceeding 100 µm, preferably not exceeding 50 µm). In order to provide a smoother blood flow path, the channels of the microvascular network may feature semi-circular cross-sections, smooth bifurcations, and channel heights and widths that vary along the length of the channels. In some embodiments, the microvascular network is defined as the space between an arrangement of polymer posts.

To assemble such preferred oxygenator devices having multiple bi-layer structures into one functional unit, the layers that include the microvascular networks are fluidically connected with each other, as are the layers that define the oxygen-supply channels. In some embodiments, this is accomplished by through-holes that penetrate the stack perpendicular to the layers. In other embodiments, the ports (i.e., the channel ends) of the layers are connected via a distribution manifold, which may have a low fluid volume, thereby contributing to a low prime volume of the assembled device. (The "prime volume" of an ECMO device is the total amount of fluid required to fill up the blood-carrying components of the device, i.e., the blood channels, chambers, internal connections, manifolds, etc.) In certain embodiments, oxygenator devices achieve prime volumes of between about 4 mL and about 10 mL. Further, at a blood flow rate of about 100 mL/min, oxygen transfer rates in the device can exceed 4 mL/min.

One preferred feature for a clinical scale oxygenator device includes blood flow channels in the first micropatterned polymer layers that are sufficient in size and number to transmit blood at a rate of about 1 L/min, while providing a oxygen transfer rate of about 50 mL/min. To achieve this feature, it is contemplated that the device may comprise about 50 to 100 bi-layers, with each bi-layer measuring approximately 4 inches square.

Accordingly, one aspect of the invention provides a method for transferring a gas to blood. The methods comprises passing blood through an oxygenator device described herein, such as any of the oxygenator devices described in Sections I-VIII, having a gas in at least channel in the second micropatterned polymer layer, to thereby transfer said gas to the blood. In certain embodiments, said gas comprises oxygen. In certain embodiments, the oxygenator device is fluidly connected to the blood vasculature of a patient. In certain embodiments, the method further comprises transferring a gas dissolved in said blood to a channel in the second micropatterned polymer layer in the oxygenator device.

X. DEFINITIONS

To facilitate an understanding of the present invention, a number of terms and phrases are defined below.

The terms "a," "an" and "the" as used herein mean "one or more" and include the plural unless the context is inappropriate.

While the invention has been particularly shown and described with reference to specific embodiments above, it should be understood by those skilled in the art that various changes in form and detail may be made therein without departing from the spirit and scope of the invention as defined by the appended claims. For example, membrane materials other than PDMS that also exhibit high gas permeability may be used. Further, the oxygenator may be integrated into a device that also encompasses other functions, such as blood filtration to augment renal and other organ functions. The scope of the invention is indicated by the appended claims, and all changes which come within the meaning and range of equivalency of the claims are intended to be embraced.

EXAMPLES

The invention now being generally described, will be more readily understood by reference to the following examples, which are included merely for purposes of illustration of certain aspects and embodiments of the present invention, and are not intended to limit the invention.

Example 1

Preparation and Testing of a First Set of Exemplary Oxygenator Devices

A parallel plate multilayered silicone-based microfluidic device containing branched microvascular networks separated from oxygen channels by thin non-porous PDMS membranes with high gas permeance was constructed. The network design utilizes a biomimetic flow pattern in small channels to reduce both the fluid forces on the blood in the channels and the overall volume of the device. The device maximizes gas transfer efficiency by incorporating an ultra-thin membrane with high oxygen permeance and by providing a membrane-blood contact area sufficient for high levels of oxygenation without the need for large blood prime volumes. Because the membrane is thinner than those generally seen in ECMO devices, it is more gas permeable and requires less surface area for equivalent oxygen transfer. Reduced membrane area is also expected to reduce the complications associated with blood-membrane interactions, thereby lowering the risk for thrombosis and/or inflammatory responses.

Part I—Preparation of Oxygenator Device

The overall structure of the oxygenator device was based on a scaling strategy in which individual blood-gas subunits are stacked to increase the capacity of the device. Each blood-gas subunit represents a bi-layer consisting of a vascular channel network for blood flow separated by a thin membrane from an oxygen channel. With an arrangement of alternating vascular and oxygen channels, the overall device utilizes the high surface area to volume ratio of each vascular layer in a larger overall network, allowing a higher volume of blood to be processed in one cycle. Each vascular channel network receives oxygen from oxygen channels situated above and below it, doubling the transfer capacity of the device.

Figure 8A:
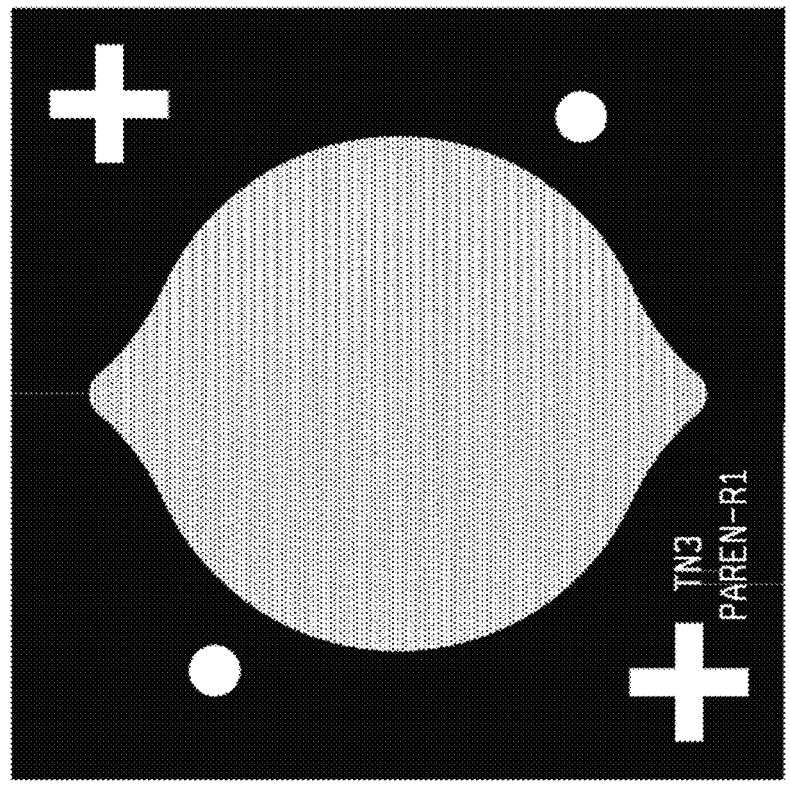
FIG. 8 illustrates the layout of mask designs for (a) a microvascular network mold, and (b) an oxygen supply channel mold. Working medium flows in through access ports at the upper right, distributes throughout the channels, and exits through another access port at the lower left. Similarly, the oxygen channel features an inlet at the top, and outlet at the bottom of the channel. The two mask designs feature alignment marks in the corners, as well as circular marks to indicate hole punching sites for interlayer fluid exchange.

The vascular channel networks were designed to eliminate areas of disturbed blood flow by implementing a series of bifurcating channels of varying widths and lengths that mimic the scaling laws seen in physiologic vasculature. By creating a fluid path that incorporates smooth bifurcations and uniform fluid distribution, the wall shear stress along the channel is more controlled compared to typical microfluidic devices or blood-flowing devices using large, open manifolds. The specific proportions of the multiple-width bifurcating channel network were selected to mimic design rules for natural vasculature and ensure smooth transitions. These design rules are based upon principles such as Murray's Law, which states that the sum of the cubes of the diameters of two daughter vessels at a bifurcation is equal to the cube of the diameter of the parent vessel. Other physiological considerations such as the nature of the velocity profile, smoothness of blood flow, and control of oxygen distribution are also reflected in the design of the bifurcation angles and channel dimensions. An illustration of the mask design for the vascular network is shown in FIG. 8(a).

For ease of fabrication, channels with rectangular cross sections were chosen for the vascular microchannel network. Rectangular channels in the device had varying widths but were designed to be 100 μm tall throughout, in order to provide a small total volume for each channel and therefore reduce the diffusion distance required for oxygen and $CO_2$ transfer.

Figure 8B:
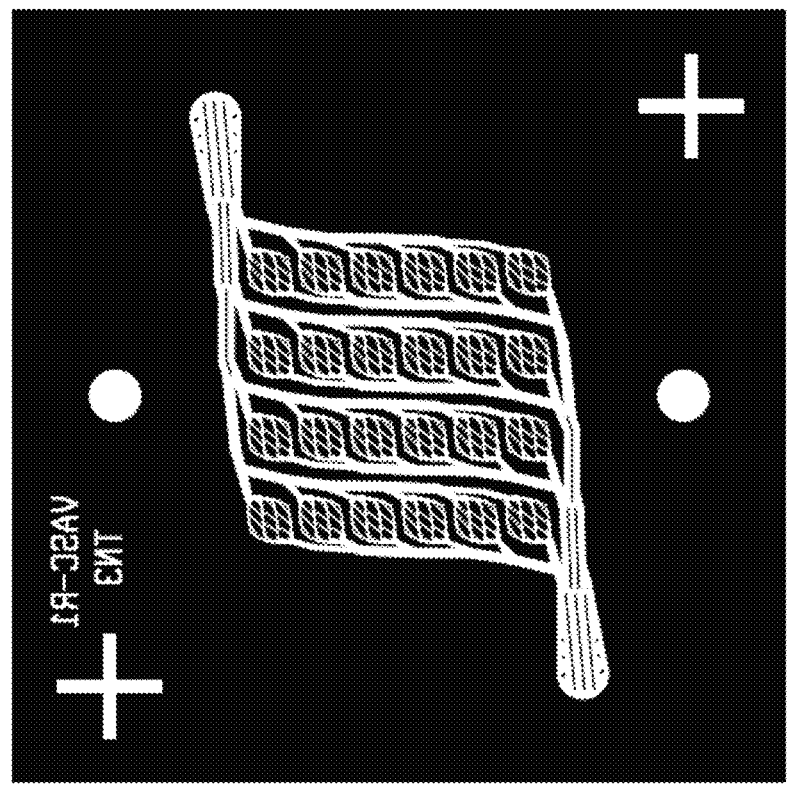

The oxygen channel, illustrated in FIG. 8(b), was designed to maximize oxygen contact area with the membrane. The channel has a total surface area of 252.97 $mm^2$, which completely overlaps and extends beyond the 85.23 $mm^2$ membrane surface area of the vascular network. For structural integrity, the oxygen channel includes 100 diameter posts throughout, spaced 100 μm apart vertically and 246 μm apart horizontally. These posts maintain the vertical gap between the oxygen channel bottom surface and the membrane. Similarly, 100 pin ribs were added to the vascular inlet and outlet ports, to avoid the possibility of membrane collapse in the wide vascular channels.

Procedures used to fabricate the oxygenator devices are described below. Using these procedures, over thirty oxygenator devices were built and tested. Devices built included those containing 3, 5, or 10 bi-layers alternating in order between oxygen channel and vascular channel. Each of the test devices built was capable of holding up to 15 psig gas-side pressure and PBS flow rates up to 10 mL/min. Most of the experiments were performed with a gas in pressure of 5 psig, and showed that the 11 μm membranes were able to withstand pressures higher than necessary for ECMO applications. Additional dye testing was done post-experimentation to verify no damage or leaks were caused by the tests.

A. Casting the Channel Layers

Channel molds were built using MEMS fabrication technology, based on procedures described in, for example, Borenstein et al. in *Biomed. Microdevices* (2002) vol. 4, 167; and Leclerc et al. in *Biomed. Microdevices* (2003) vol. 5, 109. Using this method, silicon wafers were photolithographically patterned with the microchannel design using SU-8 negative photoresist and a mask with our specified design. These were then passivated with $C_4F_8$ and used as the mold from which our devices were cast.

Individual vascular and oxygen channel layers were made by mixing PDMS elastomer and curing agent (Sylgard 184, Dow Corning, Midland, Mich.) in a 10:1 ratio by mass. PDMS was poured into the silicon wafer molds, degassed for approximately 30 min under 23-25 in Hg, and placed in a 65° C. oven to cure for a minimum of 3 h. All PDMS channel layers were 1 mm thick except for the layers that would be on the top and bottom of the overall device stack, which were cast to be 2.5 mm in thickness to accommodate tubing connections. After the PDMS was cured, each layer was cut to size along its edges. The bottom and top pieces were punched with a 1.5 mm biopsy punch for inlet and outlet tubing to be inserted.

B. Membrane Fabrication and Attachment

The PDMS membrane was made by spin-coating freshly-mixed PDMS onto an unpatterned, passivated silicon wafer using a Headway Research spin coater (Headway Research Inc, Garland, Tex.). A series of experiments were performed to determine the membrane thickness as a function of spin rate, and to determine how thin the membrane could be while maintaining necessary mechanical properties to withstand any pressure or flow changes. A curve was generated to characterize the dependence of membrane thickness on spin speed. The baseline membrane thickness was about 11 μm, as confirmed by optical and SEM measurements of a cross-sectioned membrane, which was obtained by spinning at a rate of 5000 RPM with a ramp rate of 1000 rpm/sec, for a 60 s cycle. The wafers with freshly spun PDMS were placed in a 65° C. oven to cure for a minimum of 45 min.

Membranes were attached to the oxygen channel layers using oxygen plasma treatment (March Plasma Systems, San Francisco, Calif.). The oxygen channel layers and the membrane (still attached to the unpatterned, passivated silicon wafer) were oxygen plasma treated at a pressure of 250 mTorr and a power of 100 W, for a total of 10 s. After treatment, the oxygen channel layer was placed onto the membrane, any bubbles were removed, and the wafer was placed into the 65° C. oven with a weight of 1-3 pounds placed on it. After approximately 30 min, the oxygen channel layers were lifted off of the wafer, along with the attached membrane. This was achieved by gently tracing the border of each thick PDMS piece with a sharp blade or very thin tweezers to cleave the attached membrane from the residual membrane on the wafer. Tweezers were then used to gently lift the PDMS oxygen channel layer, with the bonded membrane. To attach the vascular channel, the same plasma parameters were used to treat opposite side of the membrane and the channel side of the vascular layer. After plasma treatment, the two layers were bonded using aligning marks on the face of each piece for precision. The complete bi-layer was then placed in the 65° C. oven under weights. After proper attachment, each central bi-layer was punched with 4 through-holes in the inlets and outlets, which would allow both the oxygen and the vascular channels to connect with the next layer of their respective type. Gas exchange through each layer of the device was modeled using the polymer permeability constant equation (Eq. 1 below). See, for example, Yasuda in *J. Appl. Polym. Sci.* (1975) vol. 19, 2529.

$$P = \frac{V \cdot D}{SA \cdot t \cdot \Delta P}$$

Here, the permeability constant of a material P, is used to describe the relationship between the volume of gas that will transfer through the polymer V, the polymer thickness D, surface area of gas exchange (SA), time (t), and the transmembrane pressure ($\Delta P$). Using this equation, gas exchange through all layers other than the membrane was determined to be negligible.

C. General Assembly

Figure 9A:
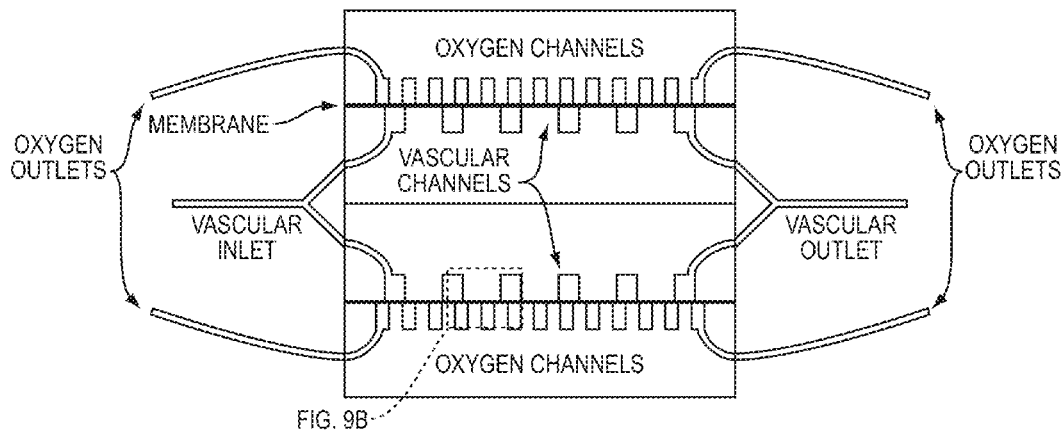
FIG. 9a illustrates a cross section of an exemplary device, built with two bi-layers stacked in a vascular-to-vascular configuration to eliminate extra oxygen transfer from the ambient environment or adjacent bi-layers.
Figure 9B:
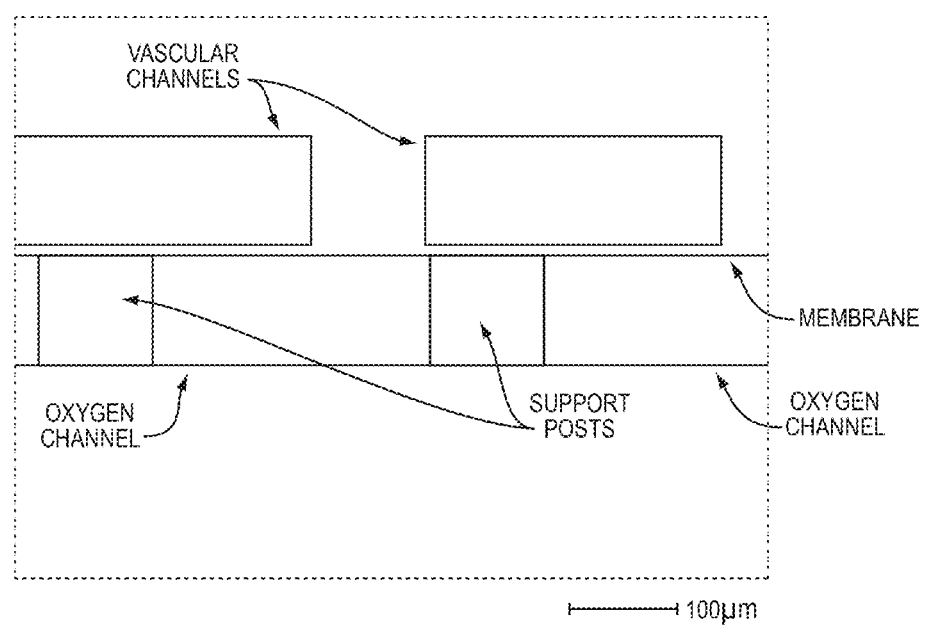
FIG. 9b is a cross section of an individual bi-layer showing vascular channels on top, above a PDMS membrane of about 10 μm, and an oxygen channel below, supported by 100 μm diameter posts.

After the individual bi-layer subunits were fabricated, they were attached to one another using the same oxygen plasma treatment parameters. Silastic Laboratory tubing (Dow Corning, Midland, Mich.) was connected to inlets and outlets of the oxygen channel. For the vascular inlets and outlets, polyetheretherketone (PEEK) tubing (Upchurch Scientific, Oak Harbor, Wash.) was used to minimize oxygen transfer through the tubing to reduce error in oxygen transfer measurements. Dow Corning 1044 Silicone Rubber RTV coating (Dow Corning, Midland, Mich.) was used to seal device-tubing interfaces to prevent leakage. For initial oxygen transfer testing, test devices were fabricated comprising two bi-layers, stacked with the two vascular channels on the inside, and the two oxygen channels on the outside. FIG. 9 depicts an assembled 2-layer test device (a), and shows a cross-sectional image of a single blood-gas bi-layer (b). The test devices were made from 2.5 mm thick PDMS pieces and were stacked vascular-to-vascular, in order to better test the gas transfer from one oxygen channel to one vascular channel through the membrane. Of course, devices are contemplated where each vascular layer will lie between two oxygen layers—this configuration is contemplated to increase the amount of oxygen transferred into each vascular channel.

Part II—Testing Oxygen Transfer Performance of Oxygenator Device

Oxygen permeance through the thin membrane of each bi-layer was evaluated by two different methods. The first set of tests characterize permeance of the PDMS membrane as a function of both the membrane thickness and the transmembrane pressure, into a static medium. The second set of experiments quantifies oxygen transfer through the membrane into a flowing liquid medium in the vascular network.

Analysis of Gas Transfer into Static Medium

Experimental Procedure:

Membrane permeance tests were performed with a protocol modeled after tests described by Burgess et al. in *Biomed. Microdevices* (2008) vol. 11, 117. A supply of oxygen was attached to the vascular channel inlet at a pre-determined pressure. The vascular outlet remained open as the vascular networks were filled with oxygen, while both gas channel inlet and outlet were clamped shut. After the vascular channels were purged with oxygen for 1-2 min, the vascular outlet was closed off using a 3-way stopcock, and the gas channel outlet was unclamped and submerged in water. Oxygen was then permitted to flow through the membrane and out of the device via the gas channel outlet, where a bubble would form in the water. A stopwatch was used to determine the time required for each bubble to form, and the average time of formation was used to determine the oxygen flow rate, ($Q_1$), based on the estimated bubble volume. Repeated observations suggested that the bubbles were of a constant volume and spherical in shape, with a diameter estimated by visual comparison with reference spheres of known size. This experiment was performed for test devices containing 11, 26, 46, 59, 83, and 120 μm thick membranes, at oxygen inlet pressures of 5 and 10 psig. Each test was run for several minutes to gather enough data for at least 4 bubbles to ensure consistency.

Figure 10:
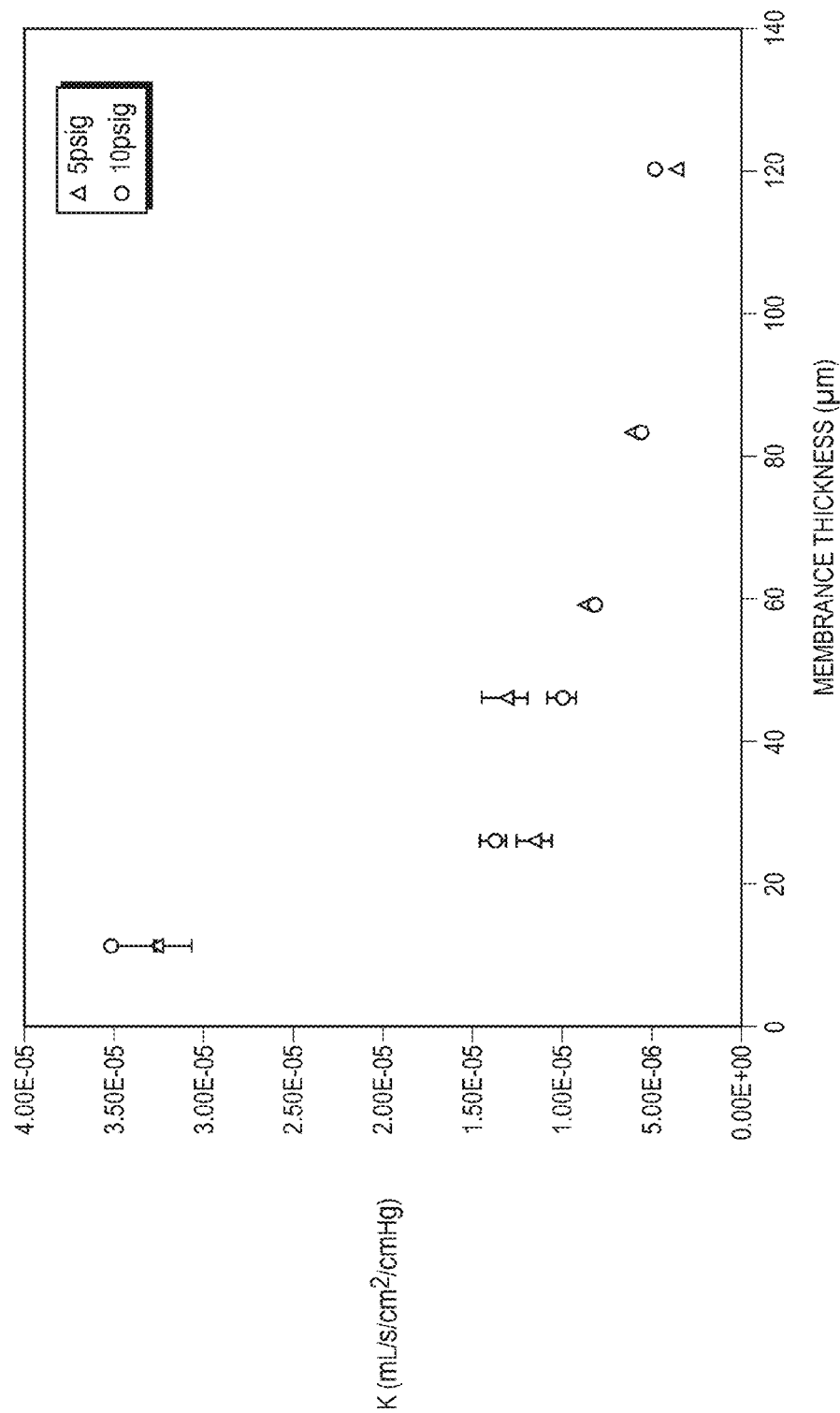
FIG. 10 is a chart of oxygen permeance (K) in mL/sec/cm$^2$/mmHg versus PDMS membrane thickness, in μm, for gas-side inlet pressures of 5 and 10 psig in devices tested in Example 1. Data reflects measurements from 4 trials. Error bars represent the standard deviation of bubble formation time (where bubble formation is used as a tracer for the amount of oxygen or air transferred across the membrane and into the PBS-containing channel), and due to the narrow range may not be visible for some data points.

Results:

Permeance of the membrane as a function of membrane thickness was examined in static test devices. The results of these experiments, summarized in FIG. 10, demonstrate that as the membrane becomes thinner, the permeance increases. To model this relationship, the permeance (K) was found for each test device, according to Eq. 2 below:

$$K = \frac{Q_2}{SA \cdot \Delta P}$$

The surface area of oxygen transfer (SA) for each device was the same. To adhere to the permeation equation conditions set forth in Yasuda in *J. Appl. Polym. Sci.* (1975) vol. 19, 2529, Q2 is defined as the actual oxygen flow rate (Q1) corrected for standard temperature and pressure. The experiments outlined were performed at transmembrane pressures ($\Delta P$) that were estimated at either 5 psig or 10 psig oxygen inlet pressure. In accordance with the predicted behavior from Eq. 2, as the transmembrane pressure doubled, the flow rate also doubled, demonstrating that K is relatively constant for each membrane thickness. For the 11 μm membrane in the devices, oxygen permeance averaged approximately $3.5 \times 10^{-5}$ mL/s/cm²/cm Hg.

Analysis of Gas Transfer into Flowing Medium

Experimental Procedure:

To assess the rate of oxygen transfer through the membrane into a flowing liquid medium in the vascular network, a second set of oxygenation tests were conducted using a blood gas analyzer. These tests were performed on phosphate buffered saline (PBS) (Invitrogen, Carlsbad, Calif.) which was initially depleted of oxygen by de-aeration in a vacuum environment for over 12 h. Though oxygenation into PBS is greatly reduced versus oxygenation into blood due to the lack of hemoglobin binding, we aimed to generate an initial model that evaluated the permeance of the PDMS membrane based on the quantity of dissolved oxygen transferred to the PBS. Prior to flow testing, each device was inspected for flow consistency by filling the vascular channels with deionized water containing food coloring for visual clarity. This test was performed on each vascular layer to ensure that there were no blockages, leaks in the membrane, or delamination of the membrane from the walls of the channels. The devices were also primed with deoxygenated PBS, and checked for absence of bubbles before any experiments were run.

A clinical blood gas analyzer (BGA) (Instrumentation Laboratory, Bedford, Mass.) was used to test the dissolved oxygen before and after each experiment. The base partial pressure of dissolved oxygen ($pO_2$) of the oxygen-depleted PBS was measured before each experiment was performed. A syringe containing deoxygenated PBS was attached to the vascular inlet tubing of a primed device and flow was administered using a Harvard syringe pump (Harvard Apparatus, Holliston, Mass.). The device was purged with 1 mL of deoxygenated PBS; flowing oxygen was then administered to the oxygen channel through the inlet at 5 psig. After the device was allowed to reach steady state, and all visual inspections confirmed the absence of any bubbles or leaks within the device, a sample was collected from the vascular outlet. A 2 mL sample of oxygenated PBS was collected using another Harvard syringe pump on the outlet vascular tubing, drawing in the oxygenated PBS at the same rate that the inlet syringe was pushing the deoxygenated PBS through. After an adequate sample was obtained, flow into the device was stopped and the $pO_2$ was tested for the oxygenated PBS sample. At the end of each experiment, the $pO_2$ was also tested in the inlet syringe to baseline passive gas transfer in the syringe. The same tests were performed using house air, (21% oxygen), and nitrogen (<0.001% oxygen) instead of oxygen for comparison.

Results:

The relationship between gas transfer into flowing PBS and residence time, as assessed by blood gas analysis of PBS, was investigated. Data from these experiments are plotted for oxygen, house air, and nitrogen gases in FIG. 11. As residence time, defined by the time that a given volume of fluid was in the gas-exchange region of the device, was increased, the oxygen transfer increased. At residence times greater than 1.4 s, the oxygen content in the output PBS exceeded the upper limit of the BGA and was not measurable. At a residence time of 1 s the oxygen content was approximately at a $pO_2$ of 570 mm Hg, which is equivalent to 17.1 mL/L according to Eq. 3 below (See Marino, in The ICU Book, ed. by B. Brown, N. Dernoski, T. Lazar (Lippincott Williams & Wilkins, Philadelphia, 1998), p. 21 L).

$$\text{Dissolved } O_2\left(\frac{mL}{L}\right) = 0.03 \times pO_2$$

Figure 11:
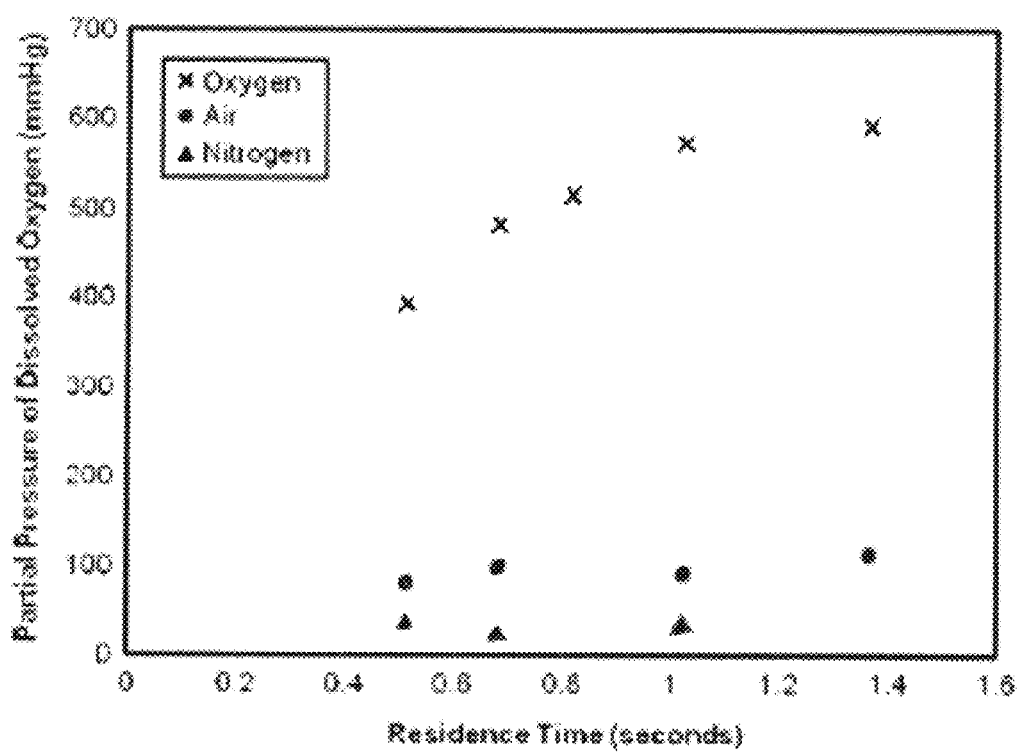
FIG. 11 is a chart of the partial pressure of oxygen dissolved in phosphate buffered saline as a function of residence time for oxygen (99.99% oxygen content), house air (21% oxygen content) and nitrogen (0% oxygen content) used as the working gas in Example 1. Each experiment was run with a consistent gas side pressure of 5 psig. The error bars represent the error in the BGA reading, which is 1 mm Hg, and may not be visible due to marker size.

Data shown in FIG. 11 represent an initial investigation of oxygen transfer in a dynamic system, which mimics the flow configuration of a blood oxygenator. In varying the PBS flow rates and the oxygen composition of the gas used, we observed the transfer of oxygen across the PDMS membrane into a flowing medium. As membrane thickness was reduced, the oxygen volume transferred was increased, but not in direct inverse proportion as seen in the static experiments. These findings suggest several complicating factors influencing gas transfer in the dynamic system, none of which are accounted for in the simple analysis used to examine the static system in the first set of experiments. These factors include variations in the dissolved oxygen concentration gradient, boundary layer effects influencing oxygen distribution in the fluid channel, fluid mechanical effects controlling the actual transmembrane pressure in a dynamic flow environment, and deformation of the membrane due to pressure variations from the gas side to the fluid side. Because of the multiple dynamic factors that a flow system introduces, the gas exchange seen in a static system cannot provide a complete model of gas exchange into flowing medium. The flow tests reveal the difference of gas transfer into a flowing channel, and enables observation of the variation in oxygen transfer that is attributed to the dynamic effects.

Example 2

Preparation and Testing of a Second Set of Exemplary Oxygenator Devices

Two additional oxygenator devices (D05 and D06) were prepared and tested. Each oxygenator device had the following features: two bi-layers made of polydimethylsiloxane, the gas-permeable membrane in each bi-layer was 11 μm thick, channels in the microvascular network (for PBS flow) had a height of 100 μm, the device was configured so that the layer containing the microvascular network for PBS flow in the first bi-layer was located adjacent to the layer containing the microvascular network for PBS flow in the second bi-layer.

Part I—Preparation of Oxygenator Device

Oxygenator devices were prepared based on procedures described above and the following general protocol.

Making Thin PDMS Membranes

First, spin a dollop (approximately the size of a half dollar) of PDMS at 5000 rpm for 60 seconds (with a ramp speed of 1000) onto a clean, coated wafer. Place the wafer in an oven at 65° C. for approximately 1 hour.

Clean a passivated wafer by removing as much of the PDMS as possible with tweezers and then spin a layer of PDMS onto the wafer at 300 rpm for 60 seconds (with a ramp speed of 300). Place the wafer in an oven at 65° C. for approximately 30 minutes, and then peel off the coating.

Casting the Pieces

Cast thin middle pieces with 6.5 g of PDMS (equivalent to ~1.0 mm; degas in desiccators—if bubbles seem trapped in PDMS, then use a nitrogen gun to interrupt the equilibrium). Next, cast thick top and bottom pieces with 20 g of PDMS (equivalent to ~2.5 mm; degas in desiccators as above). Then, bake molds in an oven at 65° C. for at least 3 hours. Cut out a circle of PDMS with an X-acto knife, and use a razor to cut along the lines of the pattern and separate the four individual pieces. Place scotch tape over top pieces to protect the channels from particles.

Modify the Middle Pieces

Using a 1 mm biopsy punch, carve out the outlet and inlet areas of all thin parenchymal and vascular pieces. Remove approximately half of the PDMS that fills these areas (~0.5 mm). When performing this procedure, use fine-tip tweezers to remove excess PDMS, then place scotch tape over the modified pieces to protect the channels from particles.

Modify the Top Pieces

Using a 1 mm biopsy punch, carve out inlet and outlet areas of the thick parenchymal as done with the middle pieces. Using a 1.5 mm biopsy punch, make two side holes in the thick vascular piece. On the vascular piece, carve out the inlet area around the punched hole and outlet area.

Modify the Bottom Pieces

Using a 1.5 mm biopsy punch, make two side holes in the thick parenchymal (one for the outlet for parenchymal, and one for the outlet for vascular; the two holes should be on the same side). On the parenchymal piece, carve out the inlet area around the punched hole and inlet area. Carve out an inlet and an outlet of the thick vascular piece. Using a 3 mm biopsy punch, make four through holes in the vascular piece.

Assemble the Middle Section

Using 5 seconds of plasma treatment, bond thin parenchymal pieces to an 11 μm thick PDMS membrane (make sure that the wafer with the membrane has been coated with Teflon). Place two large metal weights on bonded pieces for at least 5 minutes. Place blue paper in between the weights and the PDMS piece. Using flat-topped tweezers, gently scrape away thin PDMS membrane from areas surrounding the bonded parenchymal pieces. Using the tweezers, wedge one edge under the corner of the parenchymal piece and remove the piece from the wafer. The thin membrane should also peel away from the wafer in this step. Store the parenchymal pieces with the thin membrane attached membrane-side-up in a Petri dish. Using 5 seconds of plasma treatment, bond the modified vascular pieces to the parenchymal/membrane piece one-at-a-time. Use the stereoscope to align the pieces and a small Petri dish cover to support one piece as it is placed on top of the other. Place the bi-layer under two large metal weights for at least 5 minutes. Using a 3 mm biopsy punch, make four through holes in each bi-layer and then cover with tape to protect from particles. Repeat until all middle layers are aligned (N-2 middle layers are needed for an N layer device).

Next, bond two bi-layers together by exposing to five seconds of plasma treatment and aligning under the stereoscope. Neon pink poles can be used to aide in alignment by placing them into the holes of one piece and sliding the next piece on top.

Assemble the Top and Bottom Sections

Bond both top and bottom modified parenchymal pieces to an 11 μm thick PDMS membrane using 5 seconds of plasma treatment time. Place the bonded membrane and pieces under two large metal weights for at least five minutes. Remove the pieces with membrane attached as described above in the "Assemble the Middle Section." Using a 3 mm biopsy punch, make four through holes into the top parenchymal piece only. (This is the parenchymal with no side holes.) Using an X-acto knife, cut away the thin PDMS membrane blocking the two side holes and the outlet area on the bottom parenchymal piece. Using five seconds of plasma treatment, bond the respective vascular pieces one-at-a-time to the parenchymal pieces with the thin membrane attached. Place under a two large metal weights for at least five minutes.

Final Steps

Flow test the top and bottom bi-layers to test for leaks (e.g., using a low flow rate such as 0.1 mL/min, using a gloved finger, block the through holes so that the colored water flows through the channels). Dry (using, for example, an oven at 65° C.) the top and bottom pieces after flushing out all color dye. Using five seconds of plasma treatment time, bond the top bi-layer to the middle stack and then place under two large metal weights for at least five minutes. Using five seconds of plasma treatment time, bond the bottom bi-layer to the middle stack and then place under two large metal weights for at least five minutes. Cut 4 inch to 6 inch pieces of $O_4$ tubing and put them into the side holes using fine-tip tweezers. Place scotch tape on the top and bottom of the device so that there is a small amount of tape reaching over all four sides of both the top and bottom. If desired, make, print, and attach a label to the side of the device. Seal all edges and areas around the tubes with wet PDMS (use a tooth pick to spread the PDMS). Bake the device in an oven at 65° C. for at least three hours.

Part II—Testing Oxygen Transfer Performance of Oxygenator Device

Device D05 and device D06 were tested for oxygen transfer capacity to phosphate buffered saline (PBS) solution flowing through the oxygenator devices. Experimental procedures and results are provided below.

Experimental Procedure:

Oxygenator devices were prepared for transfer of oxygen to phosphate buffered saline (PBS) solution according to the procedure described in Part A below. Oxygenator devices were then tested for oxygen transfer efficiency according to the procedures described in Parts B and C below.

A. Preparation of Oxygenator Device for Transfer of Oxygen to PBS Solution

Phosphate buffered saline (PBS) was placed in a desiccator and the desiccator was placed under a vacuum for at least 10 hours. The oxygenator device was placed in the desiccator with two beakers containing the PBS. Inlet and outlet tubing of the vascular channel(s) of the oxyenator device were submerged in the PBS. Silastic tubing of the gas channel was clamped to avoid drawing air in the tubing. The desiccator was placed under vacuum. The oxygenator device (with submerged tubing) was kept in the desiccator under vacuum for at least 1.5 hours.

Approximately 30 minutes before testing the oxygenator device, the desiccator was returned to atmospheric pressure (i.e., the vacuum was released). The oxygenator device was kept in the desiccator with tubing submerged in PBS for approximately 30 minutes, until the vascular channels were completely filled with PBS. Channels in the vascular network were examined to ensure there are no bubbles. Then, the oxygenator device was removed from the desiccator while keeping the vascular tubing filled with PBS.

B. Experimental Setup

Place two syringe pumps on either side of a lab jack onto which the oxygenator device will be located. (Note: (a) both syringe pumps should be set to INFUSE>>; (b) fluid flow will go from left to right; (c) the syringe pump on the left will be referred to as Pump 1; and (d) the syringe pump on the right will be referred to as Pump 2.)

Next, place the oxygenator device onto a lab jack and connect the oxygenator device to a gas source by inserting a syringe tip into bifurcated silastic tubing. Place an empty 5 mL syringe onto Pump 2. This syringe will collect the outlet sample. Then, confirm that both pumps are set to the correct diameter (12.06 mm for BD plastic 5 mL syringes). Finally, record the temperature of the PBS samples in the desiccator.

C. Experimental Procedure

In a 5 mL syringe, collect a 5 mL aliquot of the previously prepared PBS solution (unused PBS solution should remain in the desiccator under vacuum). Measure the oxygen content of the PBS sample using a blood gas analyzer (BGA). Immediately after removing the sample from the BGA, remove any bubbles in the syringe. Then, promptly attach the syringe to the vascular inlet of the oxygenator device (note: ensure that there are no bubbles in the channel by connecting the meniscus from the syringe to the meniscus in the syringe tip of the inlet tubing). Set Pump 1 to the desired flow rate and begin to administer flow. Set Pump 2 to an identical flow rate as Pump 1. When Pump 1 has administered approximately 0.3 mL of flow through the vascular channels, turn on the gas flow. After Pump 1 has administered approximately 1.0 mL of flow through the vascular channels, attach the outlet syringe to the device and begin to collect the sample: (a) press "Stop" on Pump 1; (b) attach a syringe tip of the outlet vascular tubing onto syringe in Pump 2; and (c) press "Start" on both pumps simultaneously. After Pump 2 has collected a 2 mL sample in the outlet syringe, turn off both pumps simultaneously. Remove the syringe from Pump 2 and test the sample with the BGA (this will be the "output" data point). Finally, remove the syringe from Pump 1 and test the sample with the BGA (this will be the "inlet at end" value, and is a control value for the experiment).

Figure 12:
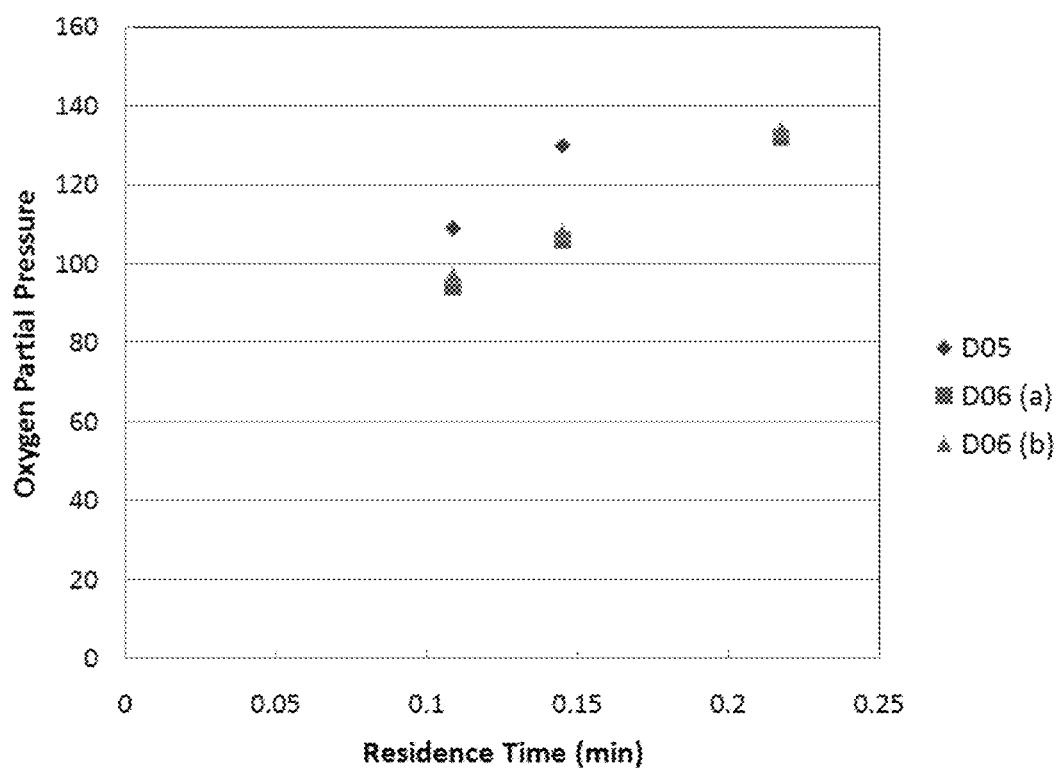
FIG. 12 is a chart showing oxygen transfer capacity for two oxygenator devices described in Example 2.
Figure 13:
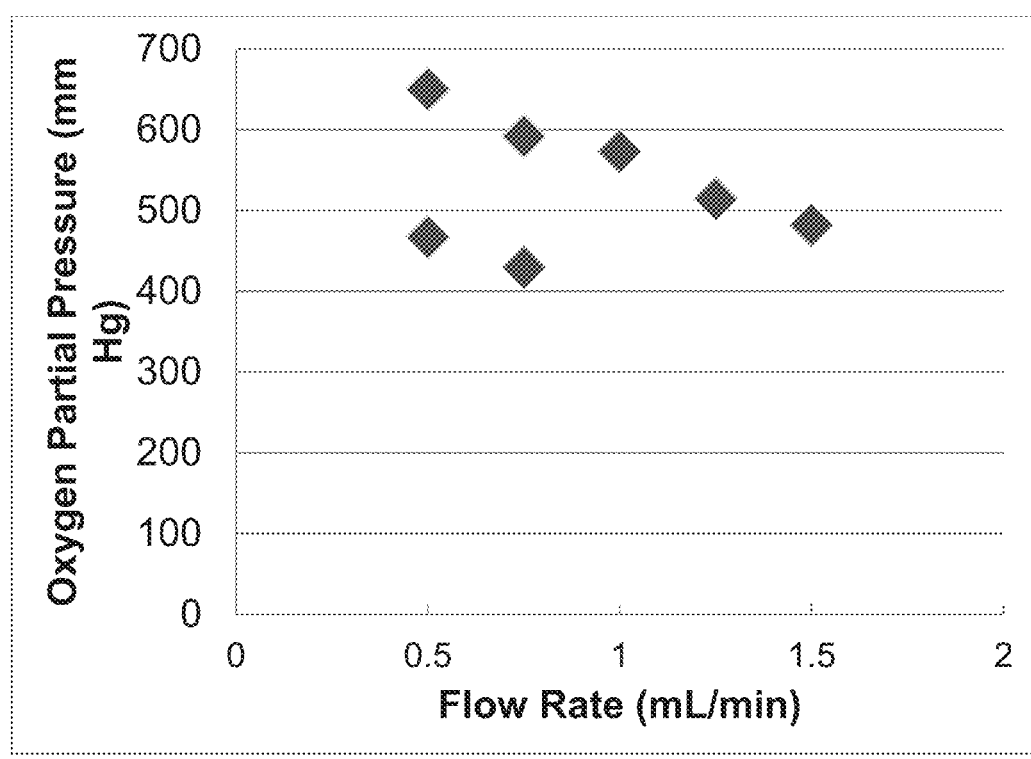
FIG. 13 is a chart showing oxygen transfer capacity for two oxygenator devices described in Example 2.

Results:

The rate of oxygen transfer from air to PBS solution flowing through the oxygenator devices as a function of residence time of the PBS solution in the oxygenator device is shown in FIG. 12. Data for the first trial using oxygenator device D06 is shown as D06 (a). Data for the second trial using oxygenator device D06 is shown as D06 (b). The rate of oxygen transfer from pure oxygen gas to PBS solution flowing through oxygenator devices D05 and D06 as a function of flow rate is shown in FIG. 13.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. An extracorporeal membrane oxygenator device, comprising a plurality of bi-layer structures arranged in a stack, each bi-layer structure comprising:
   a first polymer layer defining a plurality of blood flow channels within a surface thereof, wherein at least a subset of the plurality of blood flow channels each have a plurality of ribs running along the length of their respective blood flow channel, and wherein the length of each of the plurality of ribs is less than the total length of the respective blood flow channel along which it runs;
   a second polymer layer defining a plurality of gas flow channels within a surface thereof, wherein the second polymer layer is aligned with the first polymer layer such that the plurality of gas flow channels overlap the plurality of blood flow channels; and
   a gas permeable membrane coupled between the surface of the first polymer layer and the surface of the second polymer layer and supported by the plurality of ribs included in the subset of the plurality of blood flow channels.

2. The device of claim 1, wherein each of the plurality of ribs are about 100 µm wide.

3. The device of claim 1, wherein all of the plurality of blood flow channels each have a plurality of ribs running along at least a portion of their respective lengths.

4. The device of claim 1, wherein a height of the plurality of blood flow channels is between about 10 µm and about 150 µm.

5. The device of claim 1, wherein a height of the plurality of blood flow channels is between about 10 µm and about 50 µm.

6. The device of claim 1, wherein the plurality of gas flow channels include at least one post.

7. The device of claim 1, wherein a thickness of the gas permeable membrane is less than 10 µm.

8. The device of claim 1, wherein the width of each of the plurality of gas flow channels spans the width of multiple blood flow channels.

9. The device of claim 1, wherein the plurality of blood flow channels have a length between about 500 µm and about 3 cm.

10. The device of claim 1, further comprising:
   a third polymer layer defining a second plurality of blood flow channels within a surface thereof, a subset of the second plurality of blood flow channels each having a plurality of ribs running along at least a portion of their respective lengths;
   a fourth polymer layer defining a second plurality of gas flow channels within the surface thereof, wherein the fourth polymer layer is aligned with the third polymer layer such that the second plurality of gas flow channels overlap the second plurality of blood flow channels; and
   a second gas permeable membrane coupled between the surface of the third polymer layer and the surface of the fourth polymer layer and supported by the plurality of ribs included in the subset of the second plurality of blood flow channels.

* * * * *